US011957417B2

(12) United States Patent
Kayal et al.

(10) Patent No.: US 11,957,417 B2
(45) Date of Patent: Apr. 16, 2024

(54) SURGICAL REGISTRATION TOOLS, SYSTEMS, AND METHODS OF USE IN COMPUTER-ASSISTED SURGERY

(71) Applicant: MAKO Surgical Corp., Weston, FL (US)

(72) Inventors: Jordan Kayal, Mahwah, NJ (US); Jason Lansdown, Ridgewood, NJ (US); Eric Branch, Weston, FL (US); Ken Trimmer, Lavallette, NJ (US); Kristen Shaughnessy, Ridgewood, NJ (US)

(73) Assignee: MAKO SURGICAL CORP., Weston, FL (US)

( * ) Notice: Subject to any disclaimer, the term of this patent is extended or adjusted under 35 U.S.C. 154(b) by 0 days.

(21) Appl. No.: 17/627,538

(22) PCT Filed: Jul. 9, 2020

(86) PCT No.: PCT/US2020/041321
§ 371 (c)(1),
(2) Date: Jan. 14, 2022

(87) PCT Pub. No.: WO2021/011280
PCT Pub. Date: Jan. 21, 2021

(65) Prior Publication Data
US 2022/0265354 A1    Aug. 25, 2022

Related U.S. Application Data

(60) Provisional application No. 62/875,372, filed on Jul. 17, 2019.

(51) Int. Cl.
*A61B 34/10*    (2016.01)
*A61B 34/00*    (2016.01)
(Continued)

(52) U.S. Cl.
CPC .............. *A61B 34/10* (2016.02); *A61B 34/20* (2016.02); *A61B 34/30* (2016.02); *A61B 34/32* (2016.02);
(Continued)

(58) Field of Classification Search
CPC ......... A61B 34/10; A61B 34/20; A61B 34/30; A61B 17/175; A61B 17/155
See application file for complete search history.

(56) References Cited

U.S. PATENT DOCUMENTS 4,926,847 A * 5/1990 Luckman ............. A61B 17/155
606/88
5,037,423 A * 8/1991 Kenna .................. A61B 17/155
606/88
(Continued)

FOREIGN PATENT DOCUMENTS

WO    WO-2007030866 A1 *  3/2007  ........... A61B 17/155
WO       2017204832 A1     11/2017

OTHER PUBLICATIONS

International Search Report and Written Opinion, PCT/US2020/041321, dated Dec. 4, 2020.

*Primary Examiner* — Zade Coley
(74) *Attorney, Agent, or Firm* — Polsinelli PC

(57) ABSTRACT

A surgical registration tool including a bone engagement structure comprising a distal condyle abutment structure, at least one posterior condyle abutment structure, a side condyle abutment structure, and an anterior shaft abutment structure. The distal condyle abutment structure includes a distal planar surface. The at least one posterior condyle abutment structure includes at least one planar surface extending distally from the distal planar surface and positioned perpendicular to the distal planar surface. The side condyle abutment structure includes a planar surface extending distally from the distal planar surface and positioned
(Continued)

perpendicular to the distal planar surface and the at least one planar surface. The anterior shaft abutment structure extends distally from the distal planar surface and terminates at a distal tip. The registration tool also includes a handle coupled to the engagement structure and extending proximally therefrom, and a tracker array configured to couple to the handle.

9 Claims, 28 Drawing Sheets

(51) Int. Cl.
    *A61B 34/20*     (2016.01)
    *A61B 34/30*     (2016.01)
    *A61B 34/32*     (2016.01)
    *A61B 90/00*     (2016.01)

(52) U.S. Cl.
    CPC ........ *A61B 34/76* (2016.02); *A61B 2034/105* (2016.02); *A61B 2034/108* (2016.02); *A61B 2034/2055* (2016.02); *A61B 2034/2068* (2016.02); *A61B 2090/3916* (2016.02); *A61B 2090/3945* (2016.02); *A61B 2090/3983* (2016.02); *A61B 2090/3991* (2016.02)

(56) References Cited

U.S. PATENT DOCUMENTS

| | | | | |
|---|---|---|---|---|
| 5,234,433 A * | 8/1993 | Bert | ................ | A61B 17/8847 606/88 |
| 5,683,397 A * | 11/1997 | Vendrely | .............. | A61B 17/155 606/88 |
| 5,688,279 A * | 11/1997 | McNulty | .............. | A61B 17/155 606/88 |
| 5,720,752 A * | 2/1998 | Elliott | ................... | A61F 2/4657 606/88 |
| 7,104,997 B2 * | 9/2006 | Lionberger | .......... | A61B 17/155 606/88 |
| 7,835,778 B2 | 11/2010 | Foley et al. | | |
| 8,038,683 B2 | 10/2011 | Couture et al. | | |
| 8,403,934 B2 | 3/2013 | Angibaud et al. | | |
| 8,483,434 B2 | 7/2013 | Buehner et al. | | |
| 8,548,559 B2 | 10/2013 | Hodgson et al. | | |
| 9,005,207 B2 * | 4/2015 | Dodds | ................. | A61B 17/155 606/88 |
| 9,775,625 B2 | 10/2017 | Schoenefeld | | |
| 9,839,486 B2 | 12/2017 | Hughes et al. | | |
| 9,987,092 B2 | 6/2018 | Hladio et al. | | |
| 10,582,971 B2 | 3/2020 | Amiot et al. | | |
| 2004/0167654 A1 * | 8/2004 | Grimm | ................. | A61B 90/36 700/114 |
| 2004/0260301 A1 * | 12/2004 | Lionberger | .......... | A61B 17/155 606/88 |
| 2011/0060341 A1 * | 3/2011 | Angibaud | ............ | A61B 17/155 606/89 |
| 2014/0031829 A1 | 1/2014 | Paradis et al. | | |
| 2015/0051602 A1 * | 2/2015 | Uthgenannt | ......... | A61B 17/154 606/88 |
| 2016/0100773 A1 | 4/2016 | Ching et al. | | |
| 2018/0071031 A1 | 3/2018 | Berend et al. | | |

\* cited by examiner

FIG. 1
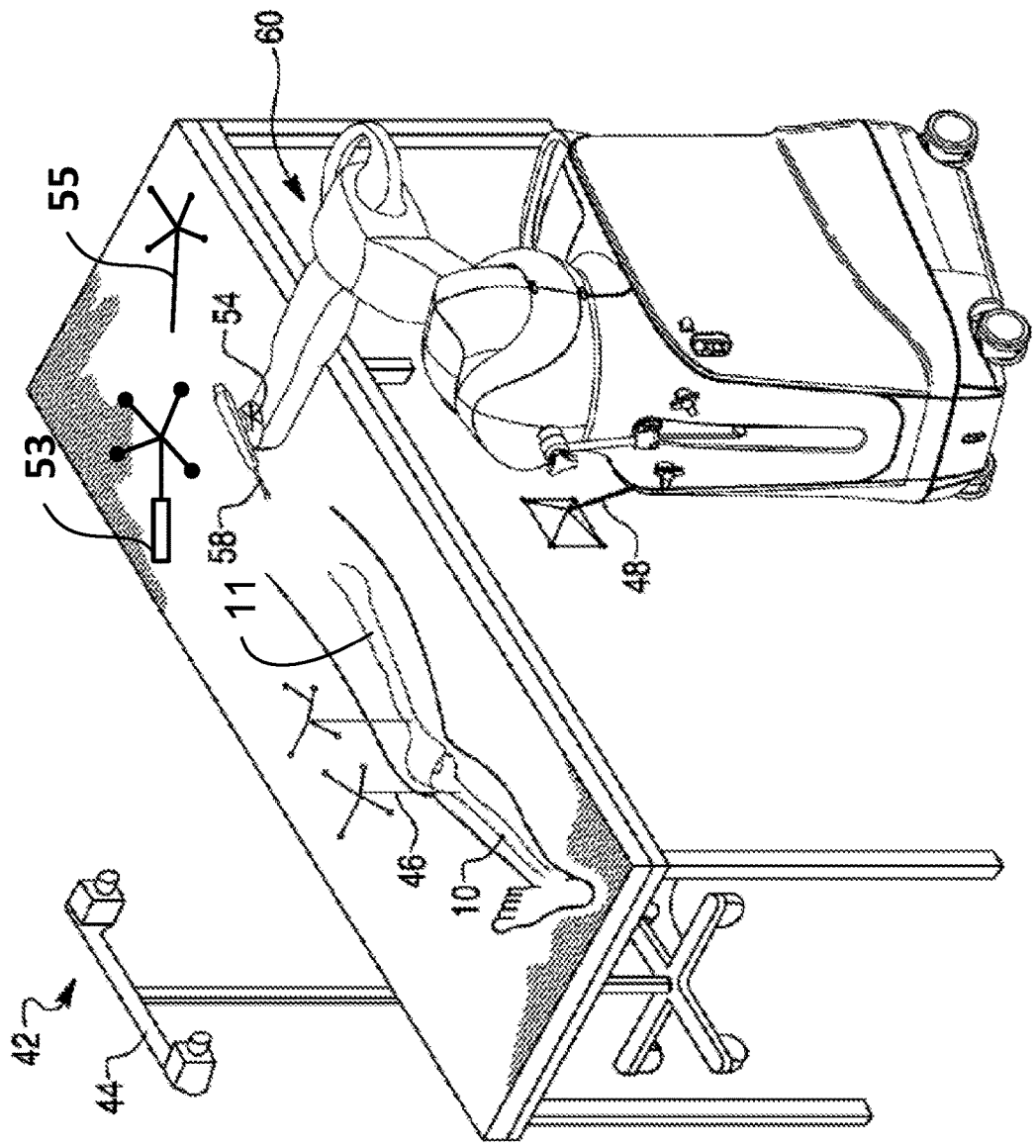
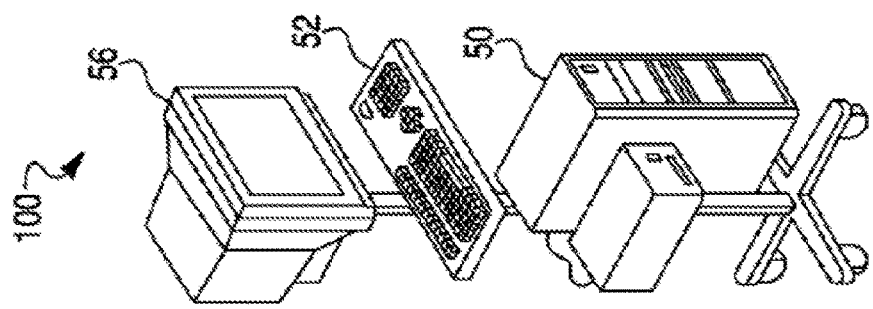

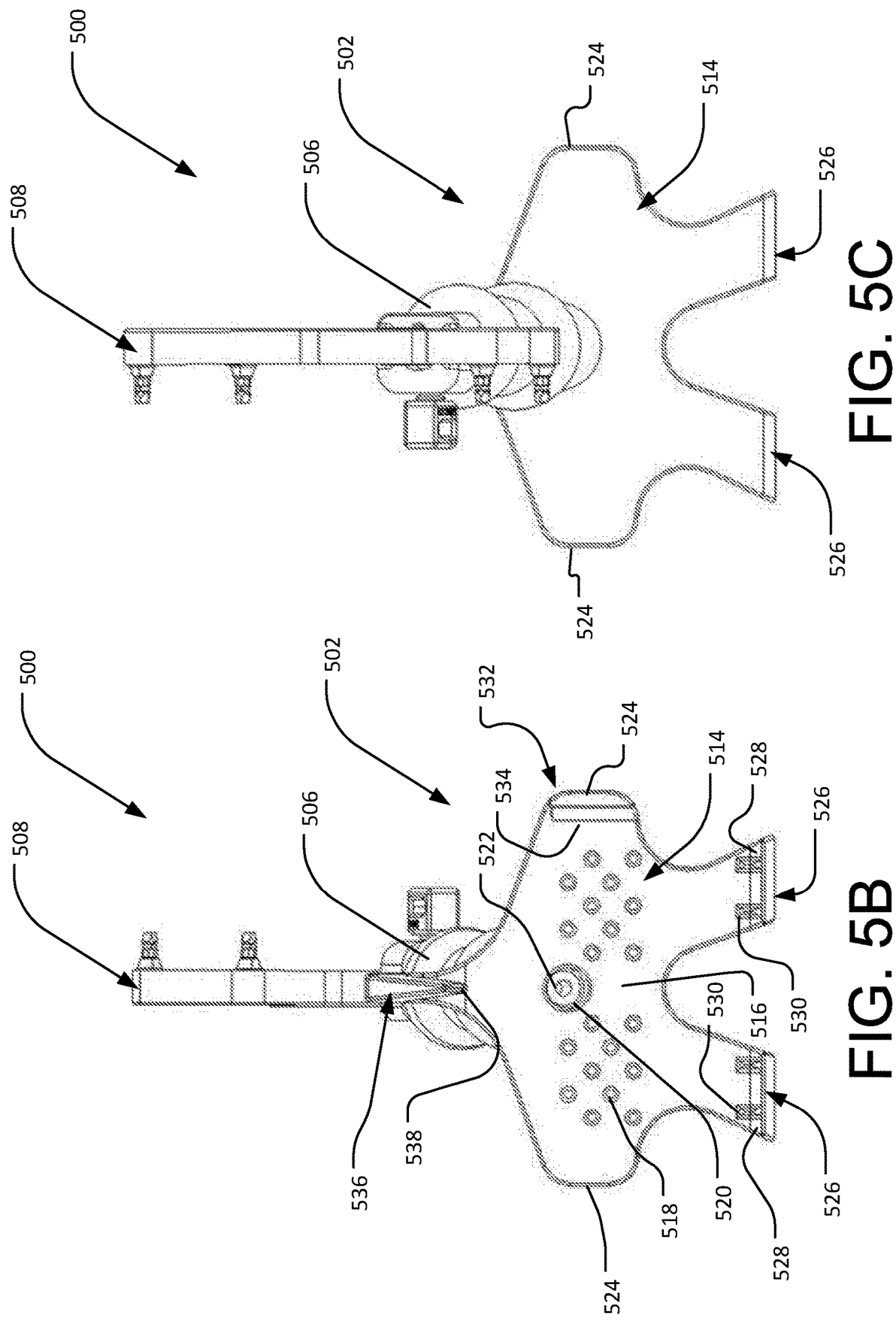

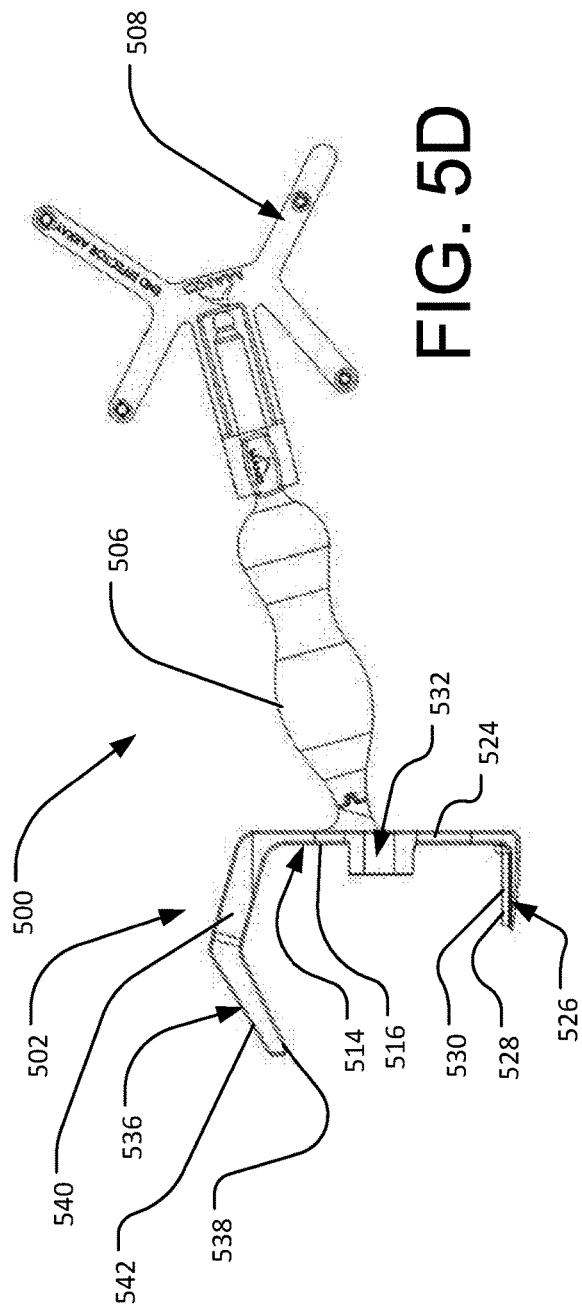
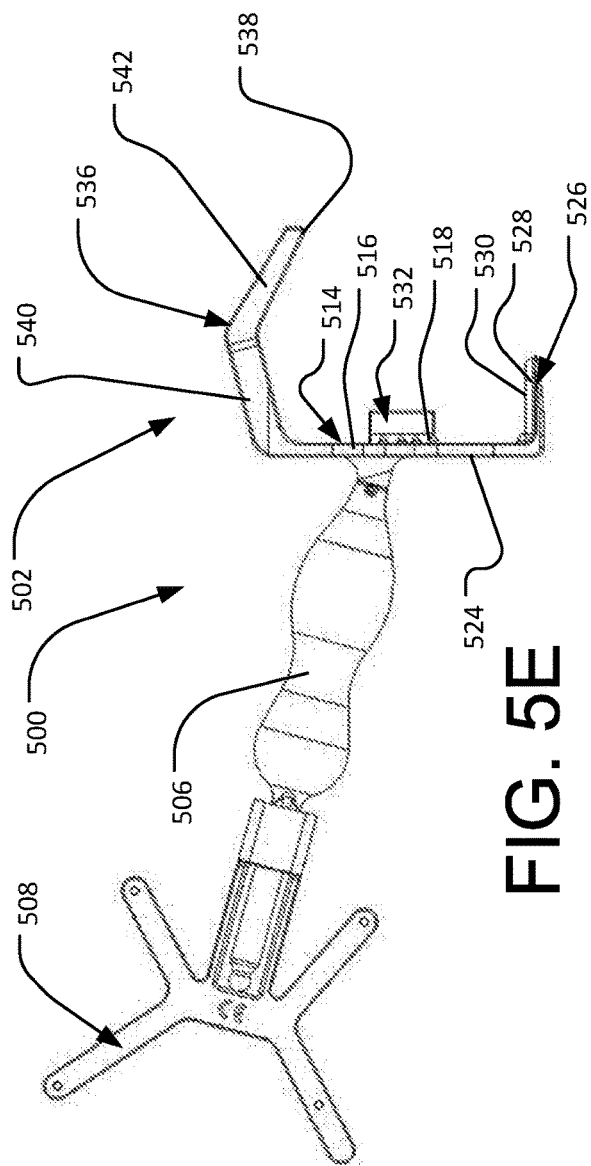

608 

Positioning Tool 500 in unique orientation on femur

608a — Contact the pair of posterior condyle facing surfaces 528 of the posterior condyle abutment structure 526 with posterior aspect of femur condyles 1a such that blades 530 cut through cartilage and contact bone 608b — Advance the tool 500 proximally relative to the distal femur condyles until the distal facing surface 516 of the distal condyle abutment structure 514 contacts the distal aspect of the femoral condyles 3a, 3b 608c — Move tool 500 medially or laterally (depending on the left or right knee at issue) until medial/lateral facing surface 534 of the medial/lateral condyle abutment structure 532 contacts the medial or lateral aspect of the knee 2

608d — Rotate tool 500 about a medial/lateral axis (transepicondylar axis) until the anterior shaft facing surface 538 of the anterior shaft abutment structure 536 contacts the anterior shaft 4 of the femur

FIG. 6B

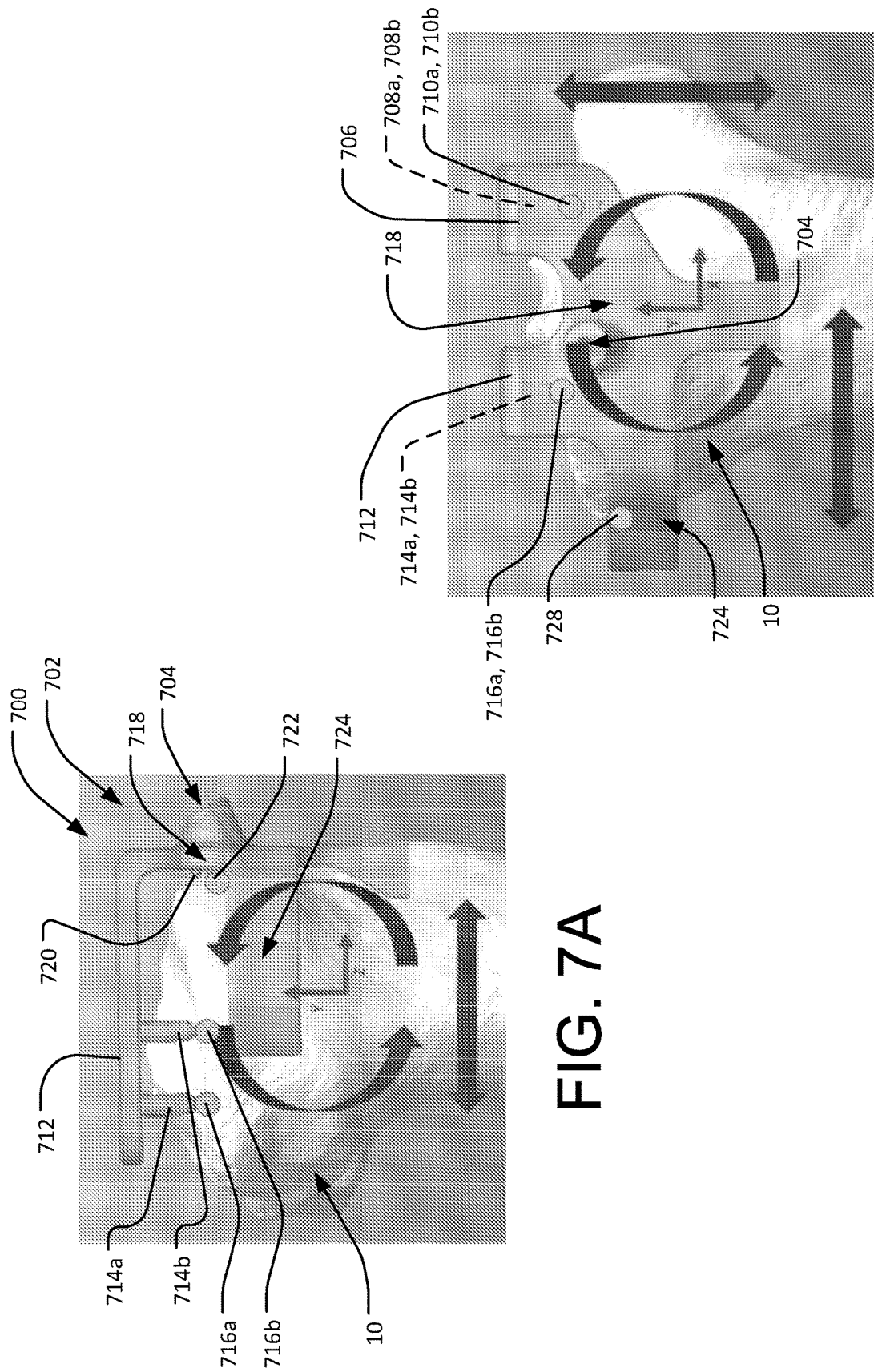

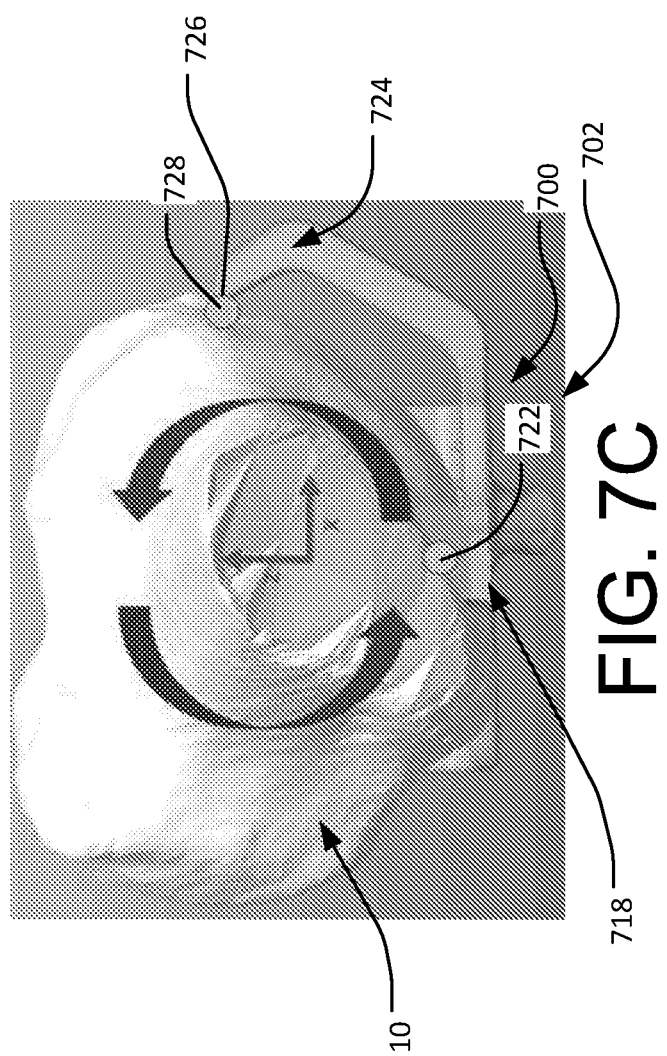

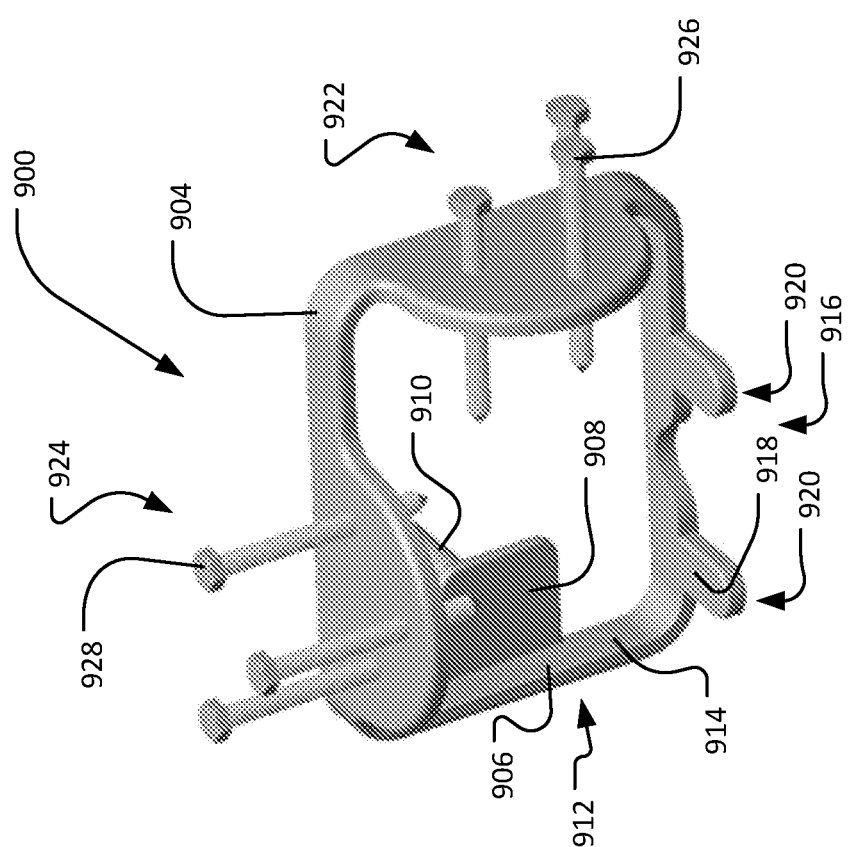

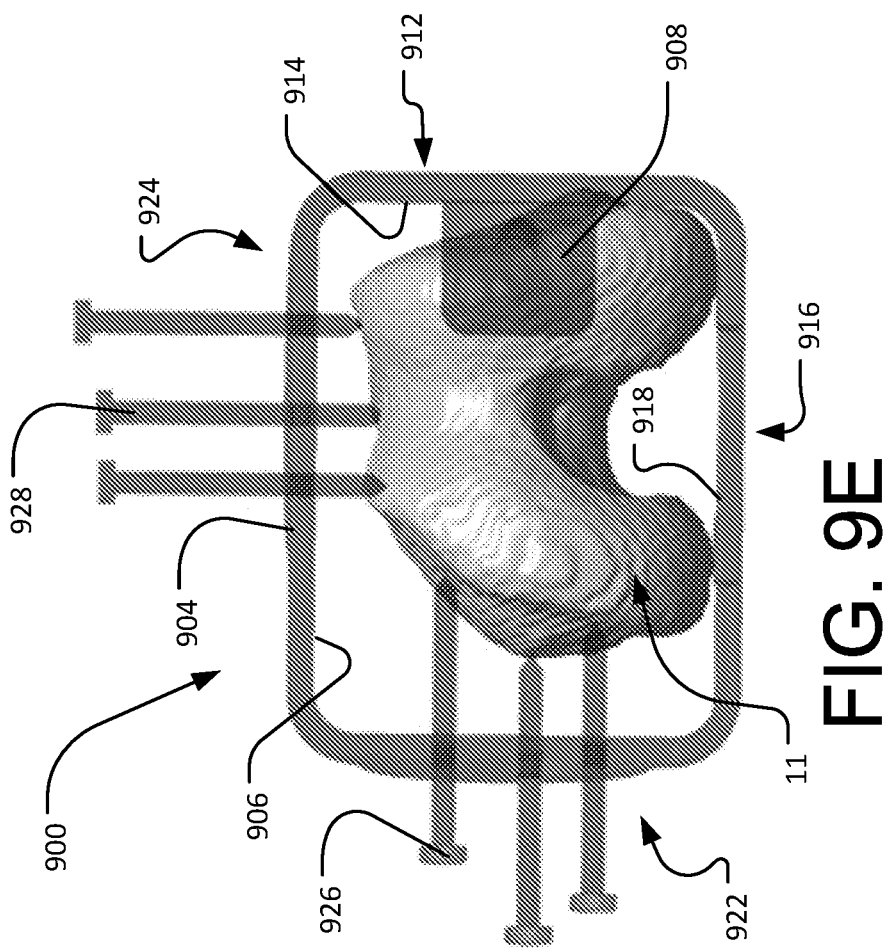

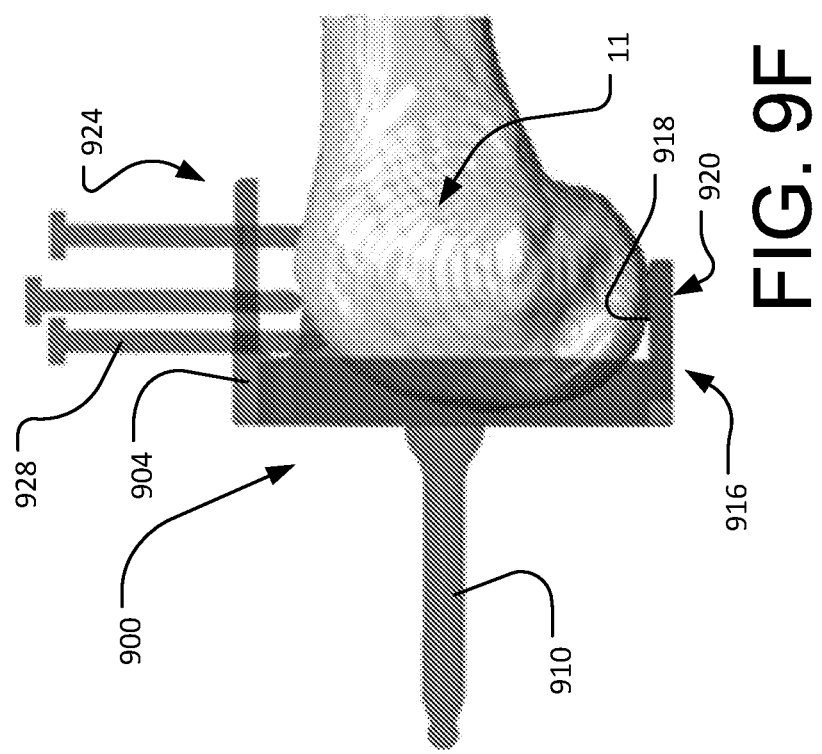

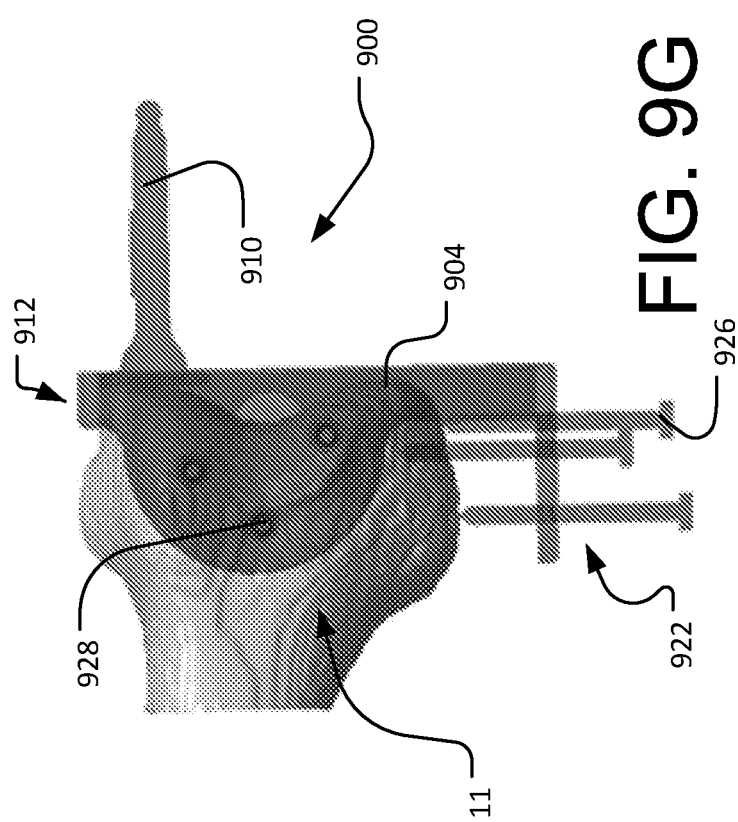

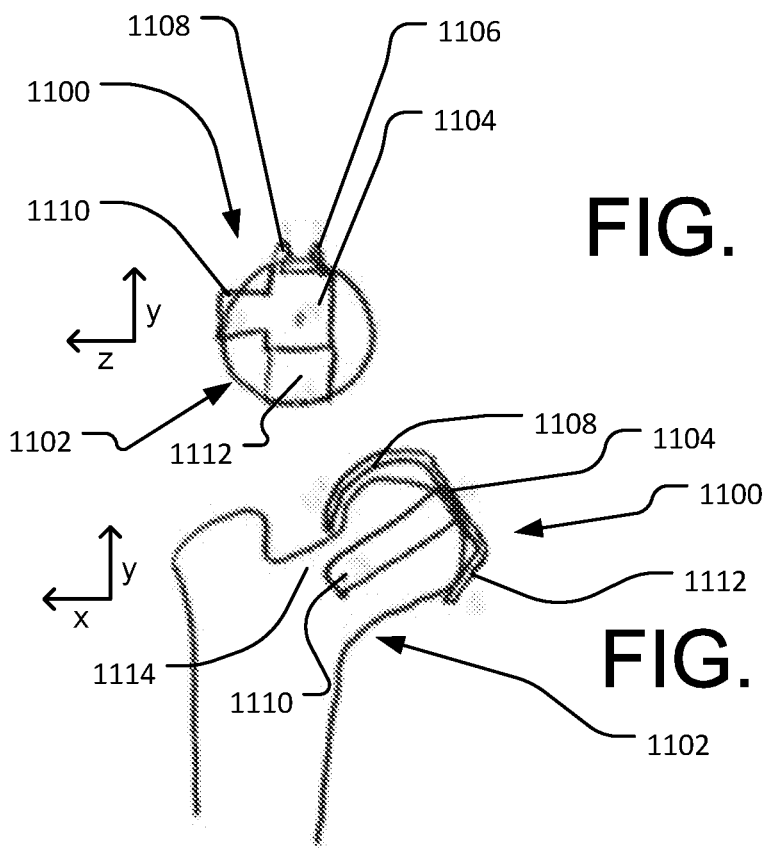
FIG. 11A
FIG. 11B
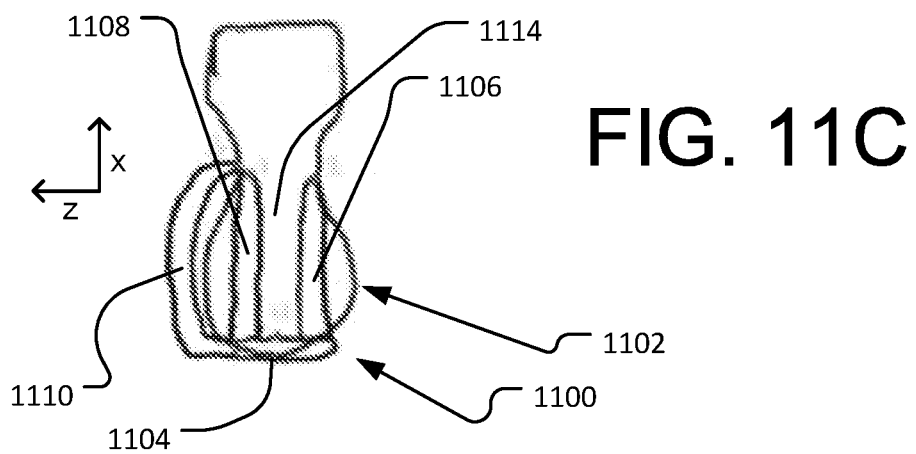
FIG. 11C

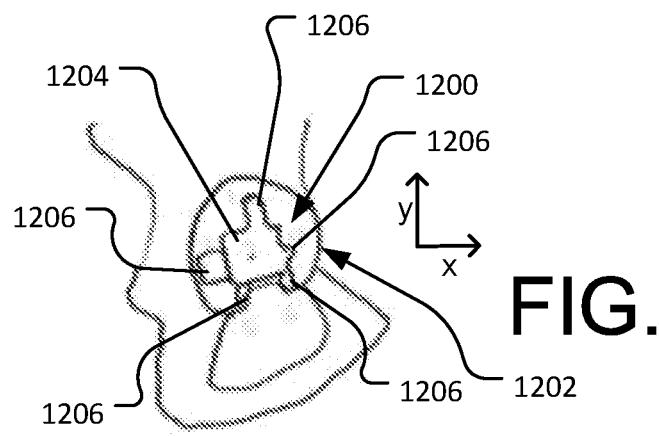
FIG. 12A
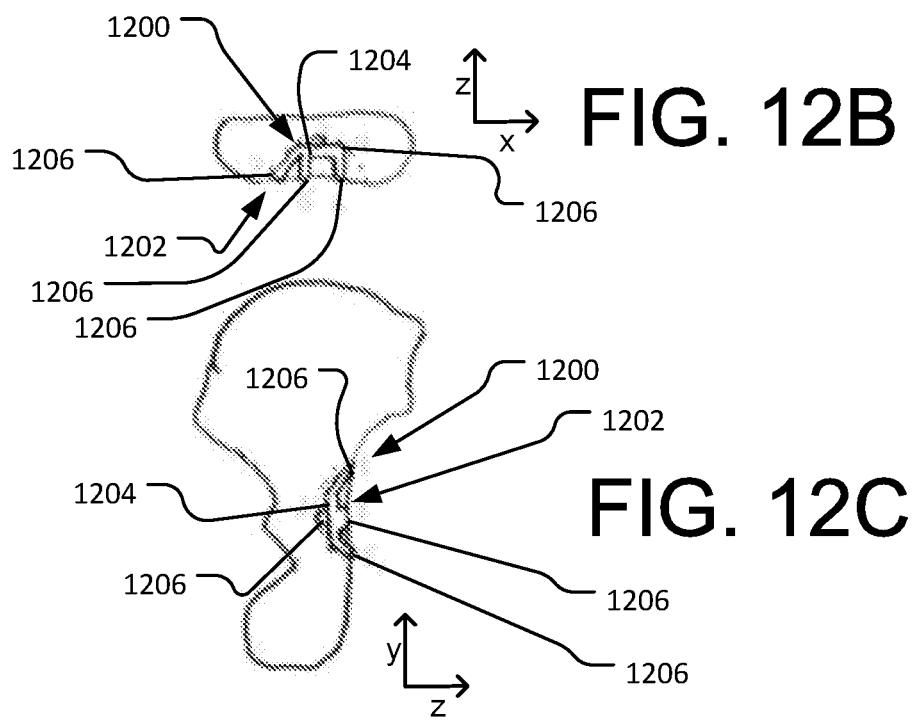
FIG. 12B
FIG. 12C

SURGICAL REGISTRATION TOOLS, SYSTEMS, AND METHODS OF USE IN COMPUTER-ASSISTED SURGERY

CROSS-REFERENCE TO RELATED APPLICATIONS

This application claims the benefit of U.S. Provisional Application No. 62/875,372, filed Jul. 17, 2019, which is hereby incorporated by reference in its entirety into the present application.

TECHNICAL FIELD

The present disclosure relates to medical systems and methods for use in computer-assisted surgery. More specifically, the present disclosure relates to surgical registration tools, systems, and methods of use in computers-assisted surgery.

BACKGROUND

Modern orthopedic joint replacement surgery typically involves at least some degree of preoperative planning of the surgery in order to increase the effectiveness and efficiency of the particular procedure. In particular, preoperative planning may increase the accuracy of bone resections and implant placement while reducing the overall time of the procedure and the time the patient joint is open and exposed.

The use of robotic systems in the performance of orthopedic joint replacement surgery can greatly reduce the intraoperative time of a particular procedure. Increasingly, the effectiveness of the procedure may be based on the tools, systems, and methods utilized during the preoperative planning stages.

Examples of steps involved in preoperative planning may involve determining: implant size, position, and orientation; resection planes and depths; access trajectories to the surgical site; and others. In certain instances, the preoperative plan may involve generating a three-dimensional ("3D"), patient specific, model of the patient bone(s) and soft tissue to undergo the joint replacement. The 3D patient model may be used as a visual aid in planning the various possibilities of implant sizes, implant orientations, implant positions, and corresponding resection planes and depths, among other parameters.

But, before the robotic system can perform the joint replacement, the robotic system and navigation system must be registered to the patient. Registration involves mapping of the virtual boundaries and constraints as defined in the preoperative plan to the patient in physical space so the robotic system can be accurately tracked relative to the patient and constrained relative to the boundaries as applied to the patient's anatomy.

While the framework for certain aspects of surgical registration may be known in the art, there is a need for tools, systems, and methods to further refine certain aspects of registration to further increase efficiency and effectiveness in robotic and robotic-assisted orthopedic joint replacement surgery.

BRIEF SUMMARY

Aspects of the present disclosure may include a surgical registration tool including a bone engagement structure comprising a distal condyle abutment structure, at least one posterior condyle abutment structure, a side condyle abutment structure, and an anterior shaft abutment structure. The distal condyle abutment structure includes a distal planar surface. The at least one posterior condyle abutment structure includes at least one planar surface extending distally from the distal planar surface and positioned perpendicular to the distal planar surface. The side condyle abutment structure includes a planar surface extending distally from the distal planar surface and positioned perpendicular to the distal planar surface and the at least one planar surface. The anterior shaft abutment structure extends distally from the distal planar surface and terminates at a distal tip. The registration tool also includes a handle coupled to the engagement structure and extending proximally therefrom, and a tracker array configured to couple to the handle. The tracker array may be configured to be tracked by a surgical navigation system.

In certain instances, when the engagements structure is used in a surgical registration on a bone including a femur, the distal planar surface may be configured to contact a distal portion of a femoral condyle, the at least one planar surface may be configured to contact a posterior portion of the femoral condyle, the planar surface may be configured to contact either a medial or lateral portion of the femoral condyle, and the distal tip may be configured to contact a shaft portion of the femur.

In certain instances, the distal condyle abutment structure may include a top side, a bottom side opposite the top side, a first side, and a second side opposite the first side, the at least one posterior condyle abutment structure extends distally from the bottom side, the side condyle abutment structure extends distally from the first side, and the anterior shaft abutment structure extends distally from the top side. In certain instances, the second side may be free from any distally extending structures.

In certain instances, the distal condyle abutment structure may include a plurality of projections extending distally from the distal planar surface configured to extend through a cartilage surface to bone.

In certain instances, the at least one posterior condyle abutment structure may include at least one longitudinal protrusion extending distally along the at least one planar surface and extending outward from the at least one planar surface. In certain instances, the at least one longitudinal protrusion may include a knife edge configured to cut through a cartilage surface to bone.

In certain instances, the at least one posterior condyle abutment structure may include a pair of posterior condyle abutment structures spaced apart from each other.

In certain instances, the distal planar surface of the distal condyle abutment structure defines a first plane, the at least one planar surface of the at least one posterior condyle abutment structure may include two planar surfaces defining a second plane, and the planar surface of the side condyle abutment structure defines a third plane, the first, second, and third planes are mutually perpendicular to each other.

In certain instances, at least one of the at least one posterior condyle abutment structure, the side condyle abutment structure, and the anterior shaft abutment structure may be adjustable in its position relative to the distal condyle abutment structure so as to accommodate bones of various sizes.

Aspects of the present disclosure may include a surgical registration tool that includes an engagement structure, a handle, and a tracker array. The engagement structure may include a trio of planar surfaces defining, respectively, three reference planes, each of the three reference plane being mutually perpendicular to each other. The trio of planar surfaces may include a distal condyle abutment surface, a posterior condyle abutment surface extending distally from the distal condyle abutment surface, and a side abutment surface extending distally from the distal condyle abutment surface. The engagement structure further may include an anterior abutment structure extending distally from the distal condyle abutment surface and terminating at a distal tip. The anterior abutment structure extends distally farther than the posterior condyle abutment surface and the side abutment surface. The handle may be coupled to the engagement structure and extend proximally therefrom. The tracker array may be configured to couple to the handle, the tracker array configured to be tracked by a surgical navigation system.

In certain instances, when the engagement structure is utilized in a surgical registration on bone including a femur, the distal condyle abutment surface may be configured to contact a distal portion of a femoral condyle, the posterior condyle abutment surface may be configured to contact a posterior portion of the femoral condyle, the side abutment surface may be configured to contact either a medial or lateral portion of the femoral condyle, and the distal tip may be configured to contact a shaft portion of the femur.

In certain instances, the distal condyle abutment surface may include a top side, a bottom side opposite the top side, a first side, and a second side opposite the first side. The posterior condyle abutment surface may extend distally from the bottom side, the side abutment surface may extend distally from the first side, and the anterior shaft abutment structure may extend distally from the top side. In certain instances, the second side may be free from any distally extending structures.

In certain instances, the distal condyle abutment surface may include a plurality of projections extending distally therefrom that may be configured to extend through a cartilage surface to bone.

In certain instances, the posterior condyle abutment surface may include at least one longitudinal protrusion extending distally thereon. In certain instances, the at least one longitudinal protrusion may include a knife edge configured to cut through a cartilage surface to bone.

In certain instances, the posterior condyle abutment surface may include a pair of posterior condyle abutment surfaces spaced apart from each other.

In certain instances, no pair of the three reference frames are parallel to each other.

In certain instances, at least one of the posterior condyle abutment surface, the side condyle abutment surface, and the anterior shaft abutment structure may be adjustable in its position relative to the distal condyle abutment surface so as to accommodate bones of various sizes.

Aspects of the present disclosure may include a system for surgical registration. The system may include a computing device including a processing device and a computer-readable medium with one or more executable instructions stored thereon. The processing device of the computing device executes the one or more instructions to perform the following operations. Receiving preoperative patient data including a patient bone model, and coordinate locations for a plurality of contact points on the patient bone model corresponding to points of virtual contact with a virtual registration tool positioned in a unique pose relative to the patient bone model. Receiving coordinate locations of a tracker array coupled to a registration tool including an engagement structure, a handle, and a tracker array. The engagement structure may include three planar contacting surfaces defining three reference planes and an extension structure extending from the three planar contacting surfaces, the extension structure configured to contact a shaft of the bone when in the unique pose. And registering the patient bone model to the patient bone.

Aspects of the present disclosure may include a system for surgical registration. The system may include a computing device including a processing device and a computer-readable medium with one or more executable instructions stored thereon. The processing device of the computing device executes the one or more instructions to perform the following operations. Receiving preoperative patient data may including a patient bone model including a bone model surface. Positioning a virtual registration tool in a unique position and orientation relative to the patient bone model in a coordinate system. The virtual registration tool may include a plurality of surfaces defining first, second, and third reference planes that intersect each other at a single point, and an extension surface. The unique position and orientation being where the bone model surface of the patient bone model abuts the plurality of surfaces and the extension surface. Storing coordinate locations for points of contact between the virtual registration tool and the patient bone model.

In certain instances, the patient bone model may include a femur bone model, and the virtual registration tool may include a distal condyle abutment structure, at least one posterior condyle abutment structure, a side condyle abutment structure, and an anterior shaft abutment structure.

In certain instances, the distal condyle abutment structure may include a distal planar surface of the plurality of surfaces. The at least one posterior condyle abutment structure may include at least one planar surface of the plurality of surfaces extending distally from the distal planar surface and positioned perpendicular to the distal planar surface. The side condyle abutment structure may include a planar surface of the plurality of planar surfaces extending distally from the distal planar surface and positioned perpendicular to the distal planar surface and the at least one planar surface. And the anterior shaft abutment structure extends distally from the distal planar surface and terminates at the extension surface.

In certain instances, the operations further include receiving coordinate locations of a tracker array coupled to a registration tool when the registration tool may be positioned on a patient bone in the unique position and orientation. The registration tool being a physical representation of the virtual registration tool. And registering the patient bone model to the patient bone.

Aspects of the present disclosure may include a computer program stored on one or more tangible, non-transitory, computer-readable storage media having executable instructions for performing the computer program on a computing system. The computer program may include receiving preoperative patient data including a patient bone model, and coordinate locations for a plurality of contact points on the patient bone model corresponding to points of virtual contact with a virtual registration tool positioned in a unique pose on the patient bone model. The computer program may also include receiving coordinate locations of a tracker array coupled to a registration tool when the registration tool may be positioned on a patient bone in the unique pose, the registration tool may include an engagement structure and a handle coupled to the tracker array, the engagement structure may include three planar contacting surfaces defining three reference planes and an extension structure extending from the three planar contacting surfaces, the extension structure configured to contact a shaft of the bone when in the unique pose. The computer program may also include registering the patient bone model to the patient bone.

Aspects of the present disclosure may include a computer-implemented method for surgical registration on a patient bone. The computer-implemented method may include receiving a patient bone model into a coordinate system, receiving a registration tool model into the coordinate system, positioning the registration tool model relative to the patient bone model as it will be used during surgical registration, the registration tool model including a plurality of planar contact surfaces, identifying coordinate locations for a plurality of contact points on the patient bone model based on virtual contact with the registration tool model, receiving coordinate locations for a tracker array coupled to a registration tool during surgical registration, and registering a coordinate system associated with the tracker array and the coordinate system. In certain instances, the registration tool model may be a virtual representation of the registration tool.

In certain instances, the patient bone model includes a femur bone model having condyles and a shaft. And the plurality of contact points on the patient bone model includes a pair of posterior contact points on a posterior aspect of the condyles of the femur bone model, at least one distal contact point on a distal aspect of the condyles of the femur bone model, a side contact point on a medial or lateral aspect of the condyles of the femur bone model, and an anterior contact point on the shaft of the femur bone model.

In certain instances, the registration tool model includes adjustable components for making virtual contact with the patient bone model. In certain instances, coordinate locations for the tracker array are received when the registration tool contacts the patient bone. In certain instances, the patient bone model includes one of a femur bone model, a tibia bone model, and a pelvic bone model.

Aspects of the present disclosure may include a surgical registration tool that includes a rigid frame. The rigid frame may include first and second planar surfaces positioned perpendicular to each other and facing inward, a third planar surface projecting inward from and being perpendicular to the first and second planar surfaces, a first adjustable section opposing the first planar surface, and a second adjustable section opposing the second planar surface. The first adjustable section may include a first plurality of adjustable members configured to extend inward and outward relative to the rigid frame so as to contact a first bone surface positioned within the rigid frame. The second adjustable section may include a second plurality of adjustable members configured to extend inward and outward relative to the rigid frame so as to contact a second bone surface positioned within the rigid frame.

In certain instances, the first plurality of adjustable members are arranged non-linearly on the first adjustable section, and the second plurality of adjustable members are arranged non-linearly on the second adjustable section. In certain instances, the registration tool may include a post extending from the third planar surface for coupling with a tracking array.

Aspects of the present disclosure may include a surgical registration tool for use on a proximal femur including a femoral head and femoral neck. The surgical registration tool may include a proximal structure, and four members extending distally from the proximal structure. The four members may include a pair of superior members, a side member oriented generally perpendicular to the pair of superior members, and an inferior member opposite the pair of superior members. The four members dimensioned and arranged to at least partially wrap around the femoral head in a unique orientation with the pair of superior members and the side member configured to contact the femoral neck.

Aspects of the present disclosure may include a surgical registration tool for use on an acetabulum including an articular surface, an acetabular fossa, an acetabular notch, and an acetabular rim. The surgical registration tool may include a central structure, and five members extending from the central structure, the five members are dimensioned and arranged to at least partially fit within the acetabulum and contact the articular surface, the acetabular fossa, the acetabular notch, and the acetabular rim in a unique and repeatable orientation.

Aspects of the present disclosure may include a registration tool for use on a tibia. The registration tool may include an engagement structure, a handle coupled to and extending from the engagement structure, and a tracker array configured to engage with the handle and be tracked in its movement by a navigation system. The engagement structure may include a lateral plateau projecting structure including at least one pin extending outward therefrom, a medial plateau projecting structure may include at least one pin extending outward therefrom, an anterior shaft abutment structure including spikes extending outward therefrom, the anterior shaft abutment structure oriented generally perpendicular to the lateral and medial plateau projecting structures, and a side projecting structure oriented generally perpendicular to the anterior shaft abutment structure and the lateral and medial plateau projecting structures. The engagement structure configured to at least partially wrap around and contact the tibia in a unique orientation.

Aspects of the present disclosure may include a method of surgical registration on a femur may include a pair of condyles and a shaft extending proximally from the pair of condyles. The method may include contacting a posterior aspect of the pair of condyles with a posterior condyle abutment structure of a registration tool. The method may further include contacting a distal aspect of the pair of condyles with a distal condyle abutment structure of the registration tool, the distal condyle abutment structure including a distal planar surface and a plurality of projections extending therefrom. The method may further include contacting a medial or lateral aspect of one of the pair of condyles with a side structure of the registration tool, the side structure including a planar surface. The method may further include, while maintaining contact between the registration tool and the posterior aspect of the condyles, the distal aspect of the pair of condyles, and the medial or lateral aspect of one of the pair of condyles, rotating the registration tool until an anterior shaft abutment structure of the registration tool contacts an anterior aspect of the shaft of the femur.

In certain instances, the method further may include registering a position and orientation of the femur with a patient bone model representative of the femur.

In certain instances, the posterior condyle abutment structure of the registration tool comprises at least one planar structure extending distally from the distal condyle abutment structure.

In certain instances, the posterior condyle abutment structure further comprises first and second blades extending upward from the at least one planar structure, the first and second blades configured to cut through cartilage to a bone surface on the posterior aspect of the pair of condyles.

In certain instances, the plurality of projections comprise spikes configured to extend through cartilage to a bone surface on the distal aspect of the pair of condyles.

In certain instances, the registration tool further comprises a handle and a tracker array.

BRIEF DESCRIPTION OF THE DRAWINGS

FIG. 1 is an illustration of a surgical system.

FIG. 5B is a front view of the registration tool.

FIG. 5C is a rear view of the registration tool.

FIG. 5D is a first side view of the registration tool.

FIG. 5E is a second side view of the registration tool.

FIG. 6B is a flowchart illustrating various steps of using the registration tool in the surgical procedure.

FIG. 7A is a side view of a tibial registration tool positioned on a tibia.

FIG. 7B is a rear view of the tibial registration tool positioned on the tibia.

FIG. 7C is a bottom view of the tibial registration tool positioned on the tibia.

FIG. 9B is a rear view of the registration tool.

FIG. 9E is a front view of the registration tool shown in phantom positioned on a femur.

FIG. 9F is a side view of the registration tool shown in phantom positioned on a femur.

FIG. 9G is a top view of the registration tool shown in phantom positioned on a femur.

FIG. 11A is a back view of a registration tool positioned on the femoral head.

FIG. 11B is a side view of the registration tool positioned on the femoral head.

FIG. 11C is a top view of the registration tool positioned on the femoral head.

FIG. 12A is back view of a registration tool positioned in the acetabulum.

FIG. 12B is top view of the registration tool positioned in the acetabulum.

FIG. 12C is side view of the registration tool positioned in the acetabulum.

DETAILED DESCRIPTION

Figure 2:
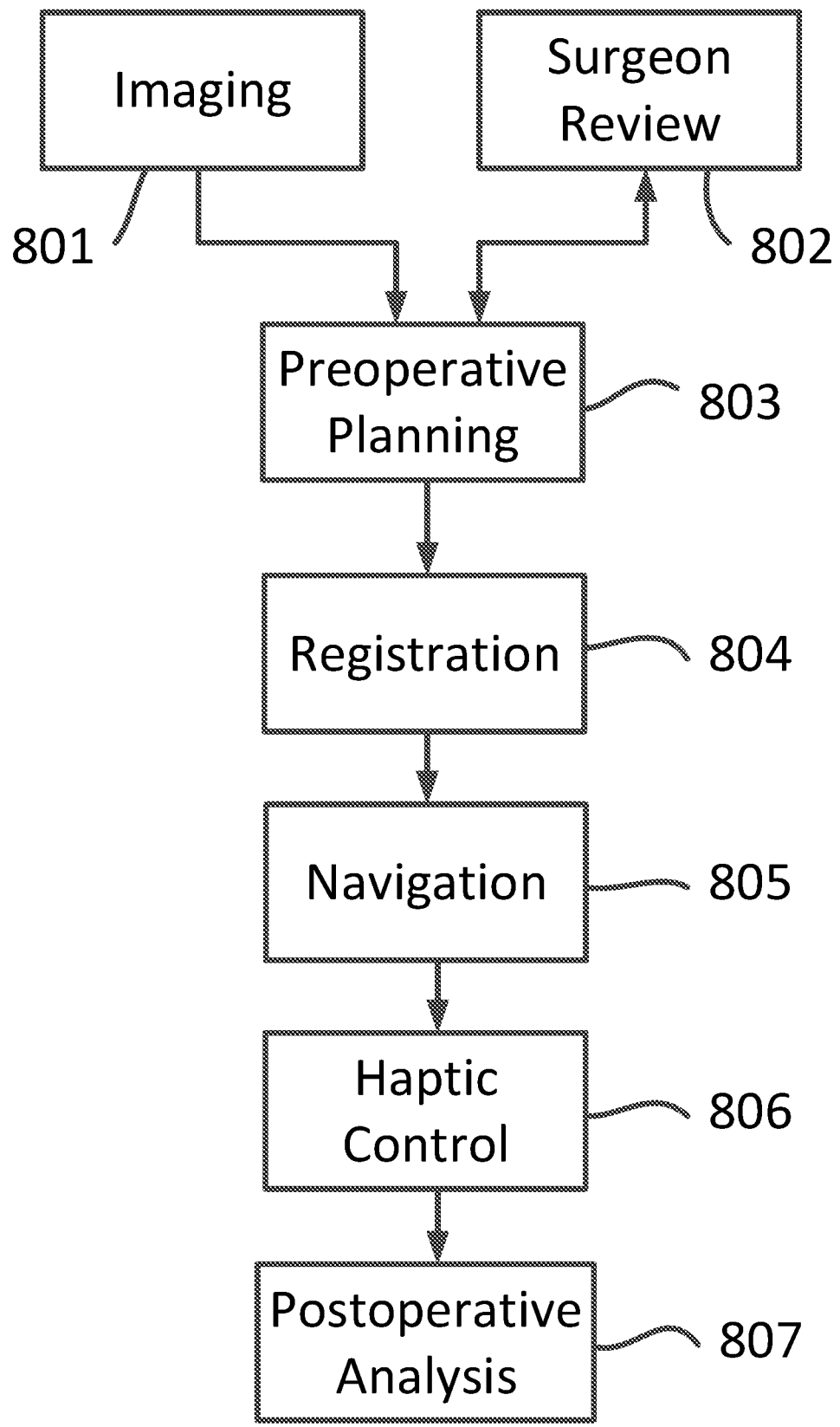
FIG. 2 is a flow chart illustrating surgical planning and performance of an arthroplasty.

The present application incorporates by reference the following applications in their entireties: International Application PCT/US2017/049466, filed Aug. 30, 2017, entitled "SYSTEMS AND METHODS FOR INTRA-OPERATIVE PELVIC REGISTRATION"; PCT/US2016/034847 filed May 27, 2016, entitled "PREOPERATIVE PLANNING AND ASSOCIATED INTRAOPERATIVE REGISTRATION FOR A SURGICAL SYSTEM"; U.S. patent application Ser. No. 12/894,071, filed Sep. 29, 2010, entitled "SURGICAL SYSTEM FOR POSITIONING PROSTHETIC COMPONENT AND/OR FOR CONSTRAINING MOVEMENT OF SURGICAL TOOL"; U.S. patent application Ser. No. 13/234,190, filed Sep. 16, 2011, entitled "SYSTEMS AND METHOD FOR MEASURING PARAMETERS IN JOINT REPLACEMENT SURGERY"; U.S. patent application Ser. No. 11/357,197, filed Feb. 21, 2006, entitled "HAPTIC GUIDANCE SYSTEM AND METHOD"; U.S. patent application Ser. No. 12/654,519, filed Dec. 22, 2009, entitled "TRANSMISSION WITH FIRST AND SECOND TRANSMISSION ELEMENTS"; U.S. patent application Ser. No. 12/644,964, filed Dec. 22, 2009, entitled "DEVICE THAT CAN BE ASSEMBLED BY COUPLING"; and U.S. patent application Ser. No. 11/750,807, filed May 18, 2007, entitled "SYSTEM AND METHOD FOR VERIFYING CALIBRATION OF A SURGICAL DEVICE".

Surgical registration tools and systems for use in conjunction with a surgical system 100 is disclosed herein. Surgical registration entails mapping of virtual boundaries, determined in preoperative planning, for example, with working boundaries in physical space. A surgical robot may be permitted to perform certain actions within the virtual boundaries, such as boring a hole or resecting a bone surface. Once the virtual boundaries are mapped to the physical space of the patient, the robot may bore the hole or resect the bone surface in a location and orientation as planned, but may be constrained from performing such actions outside the pre-planned virtual boundaries. Accurate and precise registration of the patient's anatomy allows for accurate navigation of the surgical robot during the surgical procedure. The need for accuracy and precision in the registration process must be balanced with the time required to perform the registration.

In the case of a robotically assisted surgery, virtual boundaries may be defined in the preoperative planning. In the case of a fully robotic surgery, a virtual toolpath may be defined in the preoperative planning. In either case, preoperative planning may include, for example, defining bone resection depths and identifying whether or not unacceptable notching of the femoral anterior cortex is associated with the proposed bone resection depths and proposed pose of the candidate implants. Assuming the preoperatively planned bone resection depths and implant poses are free of unacceptable notching of the femoral anterior cortex and approved by the surgeon, the bone resection depths can be updated to account for cartilage thickness by intraoperatively registering the cartilage condylar surfaces of the actual patient bones to the patient bone models employed in the preoperative planning. By so accounting for the cartilage thickness, the actual implants, upon implantation via the surgical system 100, will have their respective condylar surfaces located so as to act in place of the resected cartilage condylar surfaces of the actual patient bones. Further description of preoperative planning may be found in PCT/US2016/034847 filed May 27, 2016, entitled "PREOPERATIVE PLANNING AND ASSOCIATED INTRAOPERATIVE REGISTRATION FOR A SURGICAL SYSTEM", which is incorporated by reference in its entirety herein.

Before beginning a detailed discussion of the surgical registration and associated tools, an overview of the surgical system and its operation will now be given as follows.

I. Overview of Surgical System

To begin a detailed discussion of the surgical system, reference is made to FIG. 1. As can be understood from FIG. 1, the surgical system 100 includes a navigation system 42, a computer 50, and a haptic device 60 (also referred to as a robotic arm 60). The navigation system tracks the patient's bone (i.e., tibia 10, femur 11), as well as surgical tools (e.g., pointer device, probe, cutting tool) utilized during the surgery, to allow the surgeon to visualize the bone and tools on a display 56 during the osteotomy procedure.

The navigation system 42 may be any type of navigation system configured to track the pose (i.e. position and orientation) of a bone. For example, the navigation system 42 may include a non-mechanical tracking system, a mechanical tracking system, or any combination of non-mechanical and mechanical tracking systems. The navigation system 42 includes a detection device 44 that obtains a pose of an object with respect to a coordinate frame of reference of the detection device 44. As the object moves in the coordinate frame of reference, the detection device tracks the pose of the object to detect movement of the object.

In one embodiment, the navigation system 42 includes a non-mechanical tracking system as shown in FIG. 1. The non-mechanical tracking system is an optical tracking system with a detection device 44 and a trackable element (e.g. navigation marker 46) that is disposed on a tracked object and is detectable by the detection device 44. In one embodiment, the detection device 44 includes a visible light-based detector, such as a MicronTracker (Claron Technology Inc., Toronto, Canada), that detects a pattern (e.g., a checkerboard pattern) on a trackable element. In another embodiment, the detection device 44 includes a stereo camera pair sensitive to infrared radiation and positionable in an operating room where the arthroplasty procedure will be performed. The trackable element is affixed to the tracked object in a secure and stable manner and includes an array of markers having a known geometric relationship to the tracked object. As is known, the trackable elements may be active (e.g., light emitting diodes or LEDs) or passive (e.g., reflective spheres, a checkerboard pattern, etc.) and have a unique geometry (e.g., a unique geometric arrangement of the markers) or, in the case of active, wired or wireless markers, a unique firing pattern. In operation, the detection device 44 detects positions of the trackable elements, and the surgical system 100 (e.g., the detection device 44 using embedded electronics) calculates a pose of the tracked object based on the trackable elements' positions, unique geometry, and known geometric relationship to the tracked object. The tracking system 42 includes a trackable element for each object the user desires to track, such as the navigation marker 46 located on the bone 10. During haptically guided robotic-assisted surgeries, the navigation system may further include a haptic device marker 48 (to track a global or gross position of the haptic device 60), an end effector marker 54 (to track a distal end of the haptic device 60), a free-hand navigation probe 55 for use in the registration process, and a sleeved registration marker 53 for use with the registration tools to be described subsequently.

As indicated in FIG. 1, the surgical system 100 further includes a processing circuit, represented in the figures as a computer 50. The processing circuit includes a processor and memory device. The processor can be implemented as a general purpose processor, an application specific integrated circuit (ASIC), one or more field programmable gate arrays (FPGAs), a group of processing components, a purpose-specific processor, or other suitable electronic processing components. The memory device (e.g., memory, memory unit, storage device, etc.) is one or more devices (e.g., RAM, ROM, Flash memory, hard disk storage, etc.) for storing data and/or computer code for completing or facilitating the various processes, layers and functions described in the present application. The memory device may be or include volatile memory or non-volatile memory. The memory device may include database components, object code components, script components, or any other type of information structure for supporting the various activities and information structures described in the present application. According to an exemplary embodiment, the memory device is communicably connected to the processor via the processing circuit and includes computer code for executing (e.g., by the processing circuit and/or processor) one or more processes described herein.

The computer 50 is configured to communicate with the navigation system 42 and the haptic device 60. Furthermore, the computer 50 may receive information related to orthopedic/arthroplasty procedures and perform various functions related to performance of osteotomy procedures. For example, the computer 50 may have software as necessary to perform functions related to image analysis, surgical planning, registration, navigation, image guidance, and haptic guidance. More particularly, the navigation system may operate in conjunction with an autonomous robot or a surgeon-assisted device (haptic device) in performing the arthroplasty procedure.

The computer 50 receives images of the patient's anatomy on which an arthroplasty procedure is to be performed. Referring to FIG. 2, prior to performance of an arthroplasty, the patient's anatomy may be scanned using any known imaging technique, such as CT or MRI (Step 801) captured with a medical imaging machine. And while the disclosure makes reference to medical images captured or generated with a medical imaging machine such as a CT or MRI machine, other methods of generating the medical images are possible and contemplated herein. For example, an image of the bone may be generated intra-operatively via a medical imaging machine such as a hand-held scanning or imaging device that scans or registers the topography of the bone surface. Thus, the term medical imaging machine is intended to encompass devices of various size (e.g., C-arm, hand-held device), located at imaging centers or used intra-operatively.

Continuing on, the scan data is then segmented to obtain a three-dimensional representation of the patient's anatomy. For example, prior to performance of a knee arthroplasty, a three-dimensional representation of the femur and tibia is created. Using the three-dimensional representation and as part of the planning process, femoral and tibial landmarks can be selected, and the patient's femoral-tibial alignment is calculated along with the orientation and placement of the proposed femoral and tibial implants, which may be selected as to model and size via the computer 50. The femoral and tibial landmarks may include the femoral head center, the distal trochlear groove, the center of intercondylar eminence, the tibia-ankle center, and the medial tibial spine, among others. The femoral-tibial alignment is the angle between the femur mechanical axis (i.e., line from femoral head center to distal trochlear groove) and the tibial mechanical axis (i.e., line from ankle center to intercondylar eminence center). Based on the patient's current femoral-tibial alignment and the desired femoral-tibial alignment to be achieved by the arthroplasty procedure and further including the size, model and placement of the proposed femoral and tibial implants, including the desired extension, *varus*-valgus angle, and internal-external rotation associated with the implantation of the proposed implants, the computer 50 is programmed to calculate the desired implantation of the proposed implants or at least assist in the preoperative planning of the implantation of the proposed implants, including the resections to be made via the haptic device 60 in the process of performing the arthroplasty procedure (Step 803). The preoperative plan achieved via Step 803 is provided to the surgeon for review, adjustment and approval, and the preoperative plan is updated as directed by the surgeon (Step 802).

Since the computer 50 is used to develop a surgical plan according to Step 803, it should be understood that a user can interact with the computer 50 at any stage during surgical planning to input information and modify any portion of the surgical plan. The surgical plan may include a plurality of planned virtual boundaries (in the case of a haptic-based robotically-assisted surgery) or a tool pathway plan (in the case of an autonomous robotic surgery). The virtual boundaries or toolpaths can represent holes and/or cuts to be made in a bone 10, 11 during an arthroplasty procedure. Once the surgical plan has been developed, a haptic device 60 is used to assist a user in creating the planned holes and cuts in the bones 10, 11. Preoperative planning, especially with respect to bone resection depth planning and the prevention of femoral anterior shaft notching, will be explained more fully below.

The drilling of holes and creation of cuts or resections in bones 10, 11 can be accomplished with the assistance of a haptically guided interactive robotic system, such as the haptic guidance system described in U.S. Pat. No. 8,010,180, titled "Haptic Guidance System and Method," granted Aug. 30, 2011, and hereby incorporated by reference herein in its entirety. As the surgeon manipulates a robotic arm to drill holes in the bone or perform cuts with a high speed drill, sagittal saw, or other suitable tool, the system provides haptic feedback to guide the surgeon in sculpting the holes and cuts into the appropriate shape, which is pre-programmed into the control system of the robotic arm. Haptic guidance and feedback will be explained more fully below.

During surgical planning, the computer 50 further receives information related to femoral and tibial implants to be implanted during the arthroplasty procedure. For example, a user may input parameters of selected femoral and tibial implants into the computer 50 using the input device 52 (e.g. keyboard, mouse, etc.). Alternatively, the computer 50 may contain a pre-established database of various implants and their parameters, and a user can choose the selected implants from the database. In a still further embodiment, the implants may be custom designed based on a patient-specific surgical plan. Selection of the implants may occur during any stage of surgical planning The surgical plan may further be based on at least one parameter of the implants or a function of a parameter of the implants. Because the implants can be selected at any stage of the surgical planning process, the implants may be selected prior to or after determination of the planned virtual boundaries by the computer 50. If the implants are selected first, the planned virtual boundaries may be based at least in part on a parameter of the implants. For example, the distance (or any other relationship) between the planned virtual boundaries representing holes or cuts to made in the bones 10, 11 may be planned based on the desired varus-valgus femoral-tibial alignment, extension, internal-external rotation, or any other factors associated with a desired surgical outcome of the implantation of the arthroplasty implants. In this manner, implementation of the surgical plan will result in proper alignment of the resected bone surfaces and holes to allow the selected implants to achieve the desired surgical outcome. Alternatively, the computer 50 may develop the surgical plan, including the planned virtual boundaries, prior to implant selection. In this case, the implant may be selected (e.g. input, chosen, or designed) based at least in part on the planned virtual boundaries. For example, the implants can be selected based on the planned virtual boundaries such that execution of the surgical plan will result in proper alignment of the resected bone surfaces and holes to allow the selected implants to achieve the desired surgical outcome.

The virtual boundaries or toolpath exist in virtual space and can be representative of features existing or to be created in physical (i.e. real) space. Virtual boundaries correspond to working boundaries in physical space that are capable of interacting with objects in physical space. For example, working boundaries can interact with a surgical tool 58 coupled to haptic device 60. Although the surgical plan is often described herein to include virtual boundaries representing holes and resections, the surgical plan may include virtual boundaries representing other modifications to a bone 10, 11. Furthermore, virtual boundaries may correspond to any working boundary in physical space capable of interacting with objects in physical space.

Referring again to FIG. 2, after surgical planning and prior to performing an arthroplasty procedure, the physical anatomy (e.g. bones 10, 11) is registered to a virtual representation of the anatomy (e.g. a preoperative three-dimensional representation) using a registration technique (Step 804). Possible registration techniques include the point-based registration technique described in above-referenced U.S. Pat. No. 8,010,180, or 2D/3D registration utilizing a hand-held radiographic imaging device as described in U.S. application Ser. No. 13/562,163, titled "Radiographic Imaging Device," filed Jul. 30, 2012, and hereby incorporated by reference herein in its entirety. Registration of the patient's anatomy allows for accurate navigation during the surgical procedure (Step 805), which enables each of the virtual boundaries to correspond to a working boundary in physical space. For example, referring to FIGS. 3A and 3B, a virtual boundary 62 representing a resection in a tibia bone 10 is displayed on a computer or other display 63 and the virtual boundary 62 corresponds to a working boundary 66 in physical space 69, such as a surgery site in a surgical operating room. A portion of working boundary 66 in turn corresponds to the planned location of the resection in the tibia 10.

Figure 3B:
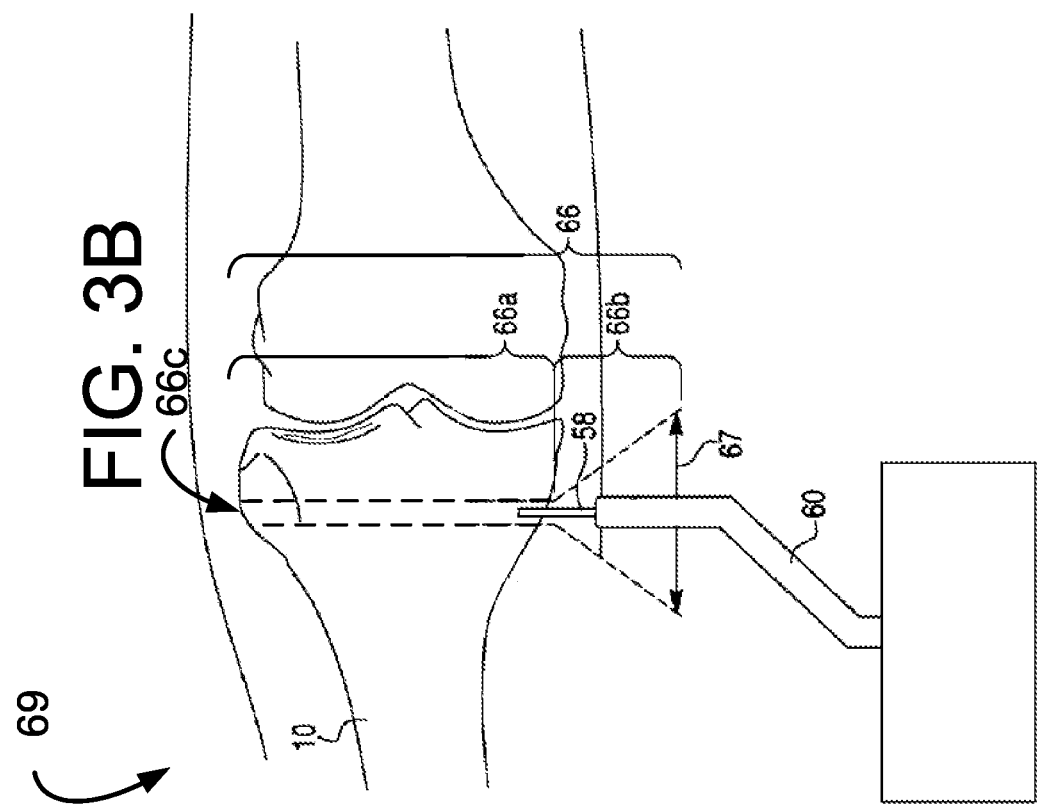
FIGS. 3A and 3B illustrate haptic guidance during performance of an arthroplasty.
Figure 3A:
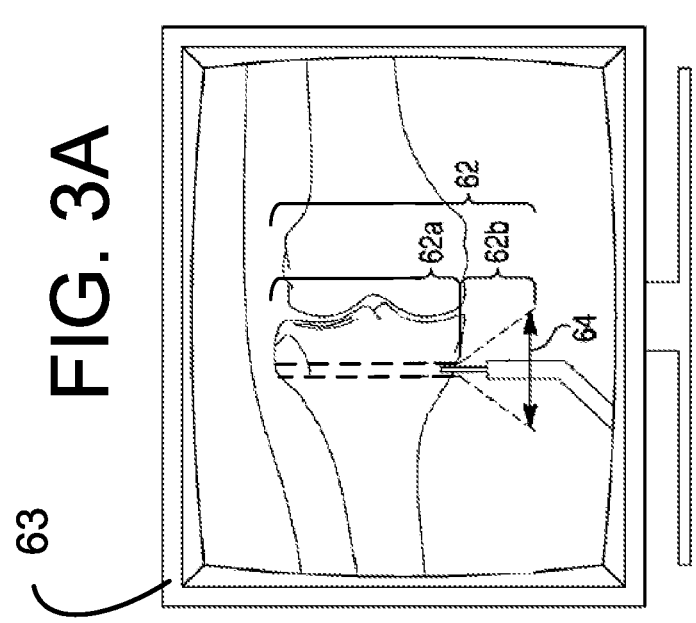

The virtual boundaries and, therefore, the corresponding working boundaries, can be any configuration or shape. Referring to FIG. 3A, virtual boundary 62 representing a proximal resection to be created in the tibia bone 10, may be any configuration suitable for assisting a user during creation of the proximal resection in the tibia 10. Portions of virtual boundary 62, illustrated within the virtual representation of the tibia bone 10, represent bone to be removed by a surgical tool. Similar virtual boundaries may be generated for holes to be drilled or milled into the tibia bone 10 for facilitating the implantation of a tibial implant on the resected tibia 10. The virtual boundaries (and therefore, the corresponding working boundaries) may include a surface or surfaces that fully enclose and surround a three-dimensional volume. In an alternative embodiment, the virtual and working boundaries do not fully enclose a three-dimensional volume, but rather include both "active" surfaces and "open" portions. For example, virtual boundary 62 representing a proximal resection in a tibia bone may have an essentially rectangular box-shaped "active" surface 62a and a collapsing funnel or triangular box-shaped "active" surface 62b connected to the rectangular box-shaped portion, with an "open" portion 64. In one embodiment, virtual boundary 62 can be created with a collapsing funnel as described in U.S. application Ser. No. 13/340,668, titled "Systems and Methods for Selectively Activating Haptic Guide Zones," filed Dec. 29, 2011, and hereby incorporated by reference herein in its entirety. The working boundary 66 corresponding to virtual boundary 62 has the same configuration as virtual boundary 62. In other words, working boundary 66 guiding a proximal resection in a tibia bone 10 may have an essentially rectangular box-shaped "active" surface 66a and a collapsing funnel or triangular box-shaped "active" surface 66b connected to the rectangular box-shaped portion, with an "open" portion 67.

In an additional embodiment, the virtual boundary 62 representing the resection in the bone 10 includes only the substantially rectangular box-shaped portion 62 *a*. An end of a virtual boundary having only a rectangular box-shaped portion may have an "open" top such that the open top of the corresponding working boundary coincides with the outer surface of the bone 10. Alternatively, as shown in FIGS. 3A and 3B, the rectangular box-shaped working boundary portion 66 *a* corresponding to virtual boundary portion 62 *a* may extend past the outer surface of the bone 10.

In some embodiments, the virtual boundary 62 representing a resection through a portion of the bone may have an essentially planar shape, with our without a thickness. Alternatively, virtual boundary 62 can be curved or have an irregular shape. Where the virtual boundary 62 is depicted as a line or planar shape and the virtual boundary 62 also has a thickness, the virtual boundary 62 may be slightly thicker than a surgical tool used to create the resection in the bone, such that the tool can be constrained within the active surfaces of working boundary 66 while within the bone. Such a linear or planar virtual boundary 62 may be planned such that the corresponding working boundary 66 extends past the outer surface of the bone 10 in a funnel or other appropriate shape to assist a surgeon as the surgical tool 58 is approaching the bone 10. Haptic guidance and feedback (as described below) can be provided to a user based on relationships between surgical tool 58 and the active surfaces of working boundaries.

The surgical plan may also include virtual boundaries to facilitate entry into and exit from haptic control, including automatic alignment of the surgical tool, as described in U.S. application Ser. No. 13/725,348, titled "Systems and Methods for Haptic Control of a Surgical Tool," filed Dec. 21, 2012, and hereby incorporated by reference herein in its entirety.

The surgical plan, including the virtual boundaries, may be developed based on information related to the patient's bone density. The density of a patient's bone is calculated using data obtained from the CT, MRI, or other imaging of the patient's anatomy. In one embodiment, a calibration object representative of human bone and having a known calcium content is imaged to obtain a correspondence between image intensity values and bone density measurements. This correspondence can then be applied to convert intensity values of individual images of the patient's anatomy into bone density measurements. The individual images of the patient's anatomy, with the corresponding map of bone density measurements, are then segmented and used to create a three-dimensional representation (i.e. model) of the patient's anatomy, including the patient's bone density information. Image analysis, such as finite element analysis (FEA), may then be performed on the model to evaluate its structural integrity.

The ability to evaluate the structural integrity of the patient's anatomy improves the effectiveness of arthroplasty planning. For example, if certain portions of the patient's bone appear less dense (i.e. osteoporotic), the holes, resections and implant placement can be planned to minimize the risk of fracture of the weakened portions of bone. Furthermore, the planned structure of the bone and implant combination after implementation of the surgical plan (e.g. the post-operative bone and implant arrangement) can also be evaluated for structural integrity, pre-operatively, to improve surgical planning. In this embodiment, holes and/or cuts are planned and the bone model and implant model are manipulated to represent the patient's bone and implant arrangement after performance of the arthroplasty and implantation procedures. Various other factors affecting the structural integrity of the post-operative bone and implant arrangement may be taken into account, such as the patient's weight and lifestyle. The structural integrity of the post-operative bone and implant arrangement is analyzed to determine whether the arrangement will be structurally sound and kinematically functional post-operatively. If the analysis uncovers structural weaknesses or kinematic concerns, the surgical plan can be modified to achieve a desired post-operative structural integrity and function.

Once the surgical plan has been finalized, a surgeon may perform the arthroplasty procedure with the assistance of haptic device 60 (step 806). Through haptic device 60, the surgical system 100 provides haptic guidance and feedback to the surgeon to help the surgeon accurately implement the surgical plan. Haptic guidance and feedback during an arthroplasty procedure allows for greater control of the surgical tool compared to conventional arthroplasty techniques, resulting in more accurate alignment and placement of the implant. Furthermore, haptic guidance and feedback is intended to eliminate the need to use K-wires and fluoroscopy for planning purposes. Instead, the surgical plan is created and verified using the three-dimensional representation of the patient's anatomy, and the haptic device provides guidance during the surgical procedure.

"Haptic" refers to a sense of touch, and the field of haptics relates to human interactive devices that provide tactile and/or force feedback to an operator. Tactile feedback generally includes tactile sensations such as, for example, vibration. Force feedback (also known as "wrench") refers to feedback in the form of force (e.g., resistance to movement) and/or torque. Wrench includes, for example, feedback in the form of force, torque, or a combination of force and torque. Haptic feedback may also encompass disabling or altering the amount of power provided to the surgical tool, which can provide tactile and/or force feedback to the user.

Surgical system 100 provides haptic feedback to the surgeon based on a relationship between surgical tool 58 and at least one of the working boundaries. The relationship between surgical tool 58 and a working boundary can be any suitable relationship between surgical tool 58 and a working boundary that can be obtained by the navigation system and utilized by the surgical system 100 to provide haptic feedback. For example, the relationship may be the position, orientation, pose, velocity, or acceleration of the surgical tool 58 relative to one or more working boundaries. The relationship may further be any combination of position, orientation, pose, velocity, and acceleration of the surgical tool 58 relative to one or more working boundaries. The "relationship" between the surgical tool 58 and a working boundary may also refer to a quantity or measurement resulting from another relationship between the surgical tool 58 and a working boundary. In other words, a "relationship" can be a function of another relationship. As a specific example, the "relationship" between the surgical tool 58 and a working boundary may be the magnitude of a haptic force generated by the positional relationship between the surgical tool 58 and a working boundary.

During operation, a surgeon manipulates the haptic device 60 to guide a surgical tool 58 coupled to the device. The surgical system 100 provides haptic feedback to the user, through haptic device 60, to assist the surgeon during creation of the planned holes, cuts, or other modifications to the patient's bone needed to facilitate implantation of the femoral and tibial implants. For example, the surgical system 100 may assist the surgeon by substantially preventing or constraining the surgical tool 58 from crossing a working boundary. The surgical system 100 may constrain the surgical tool from crossing a working boundary by any number and combination of haptic feedback mechanisms, including by providing tactile feedback, by providing force feedback, and/or by altering the amount of power provided to the surgical tool. "Constrain," as used herein, is used to describe a tendency to restrict movement. Therefore, the surgical system may constrain the surgical tool 58 directly by applying an opposing force to the haptic device 60, which tends to restrict movement of the surgical tool 58. The surgical system may also constrain the surgical tool 58 indirectly by providing tactile feedback to alert a user to change his or her actions, because alerting a user to change his or her actions tends to restrict movement of the surgical tool 58. In a still further embodiment, the surgical system 100 may constrain the surgical tool 58 by limiting power to the surgical tool 58, which again tends to restrict movement of the tool.

In various embodiments, the surgical system 100 provides haptic feedback to the user as the surgical tool 58 approaches a working boundary, upon contact of the surgical tool 58 with the working boundary, and/or after the surgical tool 58 has penetrated the working boundary by a predetermined depth. The surgeon may experience the haptic feedback, for example, as a vibration, as a wrench resisting or actively opposing further movement of the haptic device, or as a solid "wall" substantially preventing further movement of the haptic device. The user may alternatively experience the haptic feedback as a tactile sensation (e.g. change in vibration) resulting from alteration of power provided to the surgical tool 58, or a tactile sensation resulting from cessation of power provided to the tool. If power to the surgical tool is altered or stopped when the surgical tool 58 is drilling, cutting, or otherwise operating directly on bone, the surgeon will feel haptic feedback in the form of resistance to further movement because the tool is no longer able to drill, cut, or otherwise move through the bone. In one embodiment, power to the surgical tool is altered (e.g. power to the tool is decreased) or stopped (e.g. the tool is disabled) upon contact between the surgical tool 58 and a working boundary. Alternatively, the power provided to the surgical tool 58 may be altered (e.g. decreased) as the surgical tool 58 approaches a working boundary.

In another embodiment, the surgical system 100 may assist the surgeon in creating the planned holes, cuts, and other modifications to the bone by providing haptic feedback to guide the surgical tool 58 towards or along a working boundary. As one example, the surgical system 100 may provide forces to the haptic device 60 based on a positional relationship between the tip of surgical tool 58 and the closest coordinates of a working boundary. These forces may cause the surgical tool 58 to approach the closest working boundary. Once the surgical tool 58 is substantially near to or contacting the working boundary, the surgical system 100 may apply forces that tend to guide the surgical tool 58 to move along a portion of the working boundary. In another embodiment, the forces tend to guide the surgical tool 58 to move from one portion of the working boundary to another portion of a working boundary (e.g. from a funnel-shaped portion of the working boundary to a rectangular box-shaped portion of a working boundary).

In yet another embodiment, the surgical system 100 is configured to assist the surgeon in creating the planned holes, cuts, and modifications to the bone by providing haptic feedback to guide the surgical tool from one working boundary to another working boundary. For example, the surgeon may experience forces tending to draw the surgical tool 58 towards working boundary 66 when the user guides the surgical tool 58 towards working boundary 66. When the user subsequently removes the surgical tool 58 from the space surrounded by working boundary 66 and manipulates the haptic device 60 such that the surgical tool 58 approaches a second working boundary (not shown), the surgeon may experience forces pushing away from working boundary 66 and towards the second working boundary.

Haptic feedback as described herein may operate in conjunction with modifications to the working boundaries by the surgical system 100. Although discussed herein as modifications to "working boundaries," it should be understood that the surgical system 100 modifies the virtual boundaries, which correspond to the working boundaries. Some examples of modifications to a working boundary include: 1) reconfiguration of the working boundary (e.g. a change in shape or size), and 2) activating and deactivating the entire working boundary or portions of the working boundary (e.g. converting "open" portions to "active" surfaces and converting "active" surfaces to "open" portions). Modifications to working boundaries, similarly to haptic feedback, may be performed by the surgical system 100 based on a relationship between the surgical tool 58 and one or more working boundaries. Modifications to the working boundaries further assist a user in creating the required holes and cuts during an arthroplasty procedure by facilitating a variety of actions, such as movement of the surgical tool 58 towards a bone and cutting of the bone by the surgical tool 58.

In one embodiment, modifications to the working boundary facilitate movement of the surgical tool 58 towards a bone 10. During a surgical procedure, because the patient's anatomy, is tracked by the navigation system, the surgical system 100 moves the entirety of working boundary 66 in correspondence with movement of the patient's anatomy. In addition to this baseline movement, portions of working boundary 66 may be reshaped and/or reconfigured to facilitate movement of the surgical tool 58 towards the bone 10. As one example, the surgical system may tilt funnel-shaped portion 66 b of working boundary 66 relative to the rectangular box-shaped portion 66 a during the surgical procedure based on a relationship between the surgical tool 58 and the working boundary 66. The working boundary 66 can therefore be dynamically modified during the surgical procedure such that the surgical tool 58 remains within the space surrounded by the portion 66 b of working boundary 66 as the surgical tool 58 approaches the bone 10.

In another embodiment, working boundaries or portions of working boundaries are activated and deactivated. Activating and deactivating entire working boundaries may assist a user when the surgical tool 58 is approaching the bone 10. For example, a second working boundary (not shown) may be deactivated during the time when the surgeon is approaching the first working boundary 66 or when the surgical tool 58 is within the space surrounded by the first working boundary 66. Similarly, the first working boundary 66 may be deactivated after the surgeon has completed creation of a first corresponding resection and is ready to create a second resection. In one embodiment, working boundary 66 may be deactivated after surgical tool 58 enters the area within the funnel-portion leading to the second working boundary but is still outside of first funnel-portion 66 b. Activating a portion of a working boundary converts a previously open portion (e.g. open top 67) to an active surface of the working boundary. In contrast, deactivating a portion of the working boundary converts a previously active surface (e.g. the end portion 66 c of working boundary 66) of the working boundary to an "open" portion.

Activating and deactivating entire working boundaries or their portions may be accomplished dynamically by the surgical system 100 during the surgical procedure. In other words, the surgical system 100 may be programmed to determine, during the surgical procedure, the presence of factors and relationships that trigger activation and deactivation of virtual boundaries or portions of the virtual boundaries. In another embodiment, a user can interact with the surgical system 100 (e.g. by using the input device 52) to denote the start or completion of various stages of the arthroplasty procedure, thereby triggering working boundaries or their portions to activate or deactivate.

In view of the operation and function of the surgical system 100 as described above, the discussion will now turn to methods of preoperatively planning the surgery to be performed via the surgical system 100, followed by a detailed discussion of methods of registering the preoperative plan to the patient's actual bone and also to applicable components of the surgical system 100.

The haptic device 60 may be described as a surgeon-assisted device or tool because the device 60 is manipulated by a surgeon to perform the various resections, drill holes, etc. In certain embodiments, the device 60 may be an autonomous robot, as opposed to surgeon-assisted. That is, a tool path, as opposed to haptic boundaries, may be defined for resecting the bones and drilling holes since an autonomous robot may only operate along a pre-determined tool path such that there is no need for haptic feedback. In certain embodiments, the device 60 may be a cutting device with at least one degree of freedom that operates in conjunction with the navigation system 42. For example, a cutting tool may include a rotating burr with a tracker on the tool. The cutting tool may be freely manipulate-able and handheld by a surgeon. In such a case, the haptic feedback may be limited to the burr ceasing to rotate upon meeting the virtual boundary. As such, the device 60 is to be viewed broadly as encompassing any of the devices described in this application, as well as others.

After the surgical procedure is complete, a postoperative analysis (step 807) may be performed immediately or after a period of time. The postoperative analysis may determine the accuracy of the actual surgical procedure as compared with the planned procedure. That is, the actual implant placement position and orientation may be compared with the values as planned. Factors such as varus-valgus femoral-tibial alignment, extension, internal-external rotation, or any other factors associated with the surgical outcome of the implantation of the arthroplasty implants may be compared with the values as planned.

II. Preoperative Steps of Arthroplasty Procedure

The preoperative steps of an arthroplasty procedure may include the imaging of the patient and the preoperative planning process that may include implant placement, bone resection depth determination, and an anterior shaft notching assessment, among other assessments. The bone resection depth determination includes selecting and positioning three dimensional computer models of candidate femoral and tibial implants relative to three dimensional computer models of the patient's distal femur and proximal tibia to determine a position and orientation of the implants that will achieve a desirable surgical outcome for the arthroplasty procedure. As part of this assessment, the depths of the necessary tibial and femoral resections are calculated, along with the orientations of the planes of those resections.

The anterior shaft notching assessment includes determining whether or not an anterior flange portion of the three dimensional model of the selected femoral implant will intersect the anterior shaft of the three dimensional model of the patient's distal femur when the implant three dimensional model is positioned and oriented relative to the femur three dimensional model as proposed during the bone resection depth determination. Such an intersection of the two models is indicative of notching of the anterior femoral shaft, which must be avoided.

Determining bone resection depth and performing an anterior shaft notching assessment is described in PCT/US2016/034847, filed May 27, 2016, which is hereby incorporated by reference in its entirety.

A. Preoperative Imaging

In preparation for a surgical procedure (e.g., knee arthroplasty, hip arthroplasty, ankle arthroplasty, shoulder arthroplasty, elbow arthroplasty), a patient may undergo preoperative imaging at an imaging center, for example. The patient may undergo magnetic resonance imaging ("MRI"), a computed tomography ("CT") scan, a radiographic scan ("X-ray"), among other imaging modalities, of the operative joint. As seen in FIG. 4A, which is an example coronal scan of a knee, a patient joint 102 including a femur 104 and a tibia 106 may undergo a CT scan. The CT scan may include a helical scan of the knee joint 102 packaged as a Digital Imaging and Communications in Medicine ("DICOM") file. From the file, two-dimensional image slices or cross-sections are viewable in multiple planes (e.g., coronal, sagittal, axial). A segmentation process may be performed on the two-dimensional images 108 by applying a spline 110 over the bone contour line. Or, the segmentation process may be performed on the images 108 as a whole without the need to apply a spline 110 to the 2D image slices.

Figure 4C:
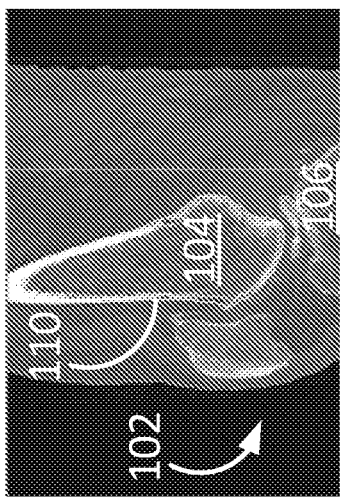
FIG. 4C is a sagittal image of a femur.
Figure 4E:
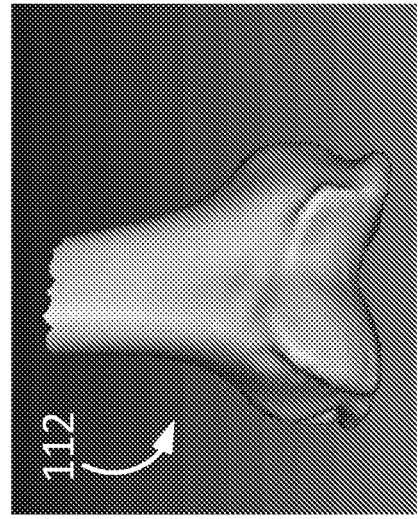
FIG. 4E is a femoral bone model.
Figure 4B:
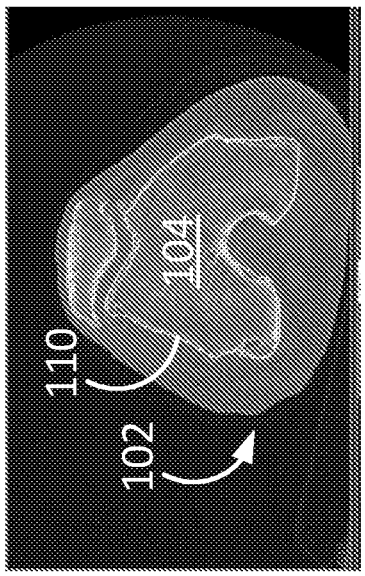
FIG. 4B is an axial image of a femur.
Figure 4D:
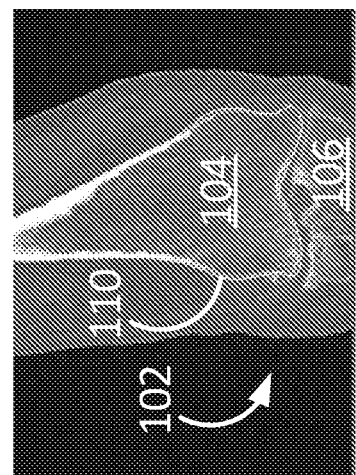
FIG. 4D is a coronal image of a knee joint.
Figure 4A:
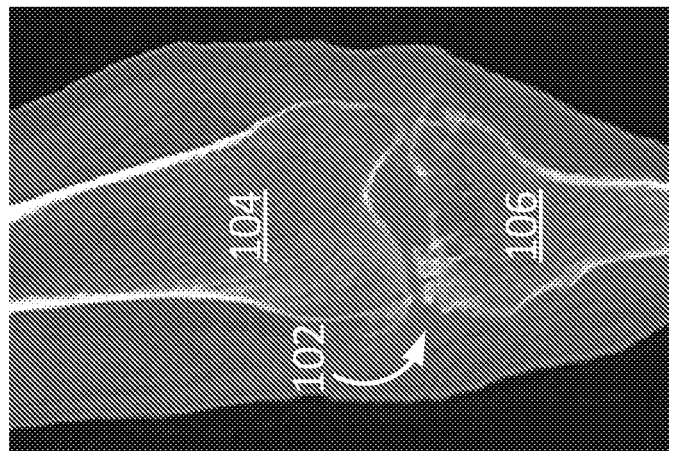
FIG. 4A is a coronal image of a knee joint.

FIGS. 4B, 4C, and 4D illustrate, respectively, an axial image 108 of the femur 104 with a spline 110 on bone surface, a sagittal image 108 of the joint 102 with a spline 110 on the bone surface of the femur 104, and a coronal image 108 of the joint 102 with a spline 110 on the femur 104. In certain instances, the segmentation process may be a manual process with a person identifying the spline 110 on each two-dimensional image slice 108. In certain instances, the segmentation process may be automated where the spline 110 is automatically applied to the bone contour line in the image slices 108. And in certain instances, the segmentation process may be a combination of manual and automatic processes.

After the segmentation process is complete, the segmented images 108 may be combined in order to generate a three-dimensional ("3D") bone model of the joint 102, including a 3D femoral model 112, and a 3D tibial model (not shown in the figures).

As seen in FIG. 4E, which is an anterior view of the 3D femoral model 112, the model 112 represents the femur 104 in a degenerated state, prior to performance of any surgical procedure to modify the bone. From this model 112, various steps of a preoperative planning process may be performed.

In certain instances, a 3D femoral model 112 of the patient joint 102 may be generated from a statistical model or generic model of the joint 102 that is morphed or otherwise modified to approximate the patient joint 102 based on certain factors that do not require segmenting the 2D image slices 108 with a spline 110. In certain instances, the segmentation process may fit a 3D statistical or generic bone model to the scanned image 108 of the femur 104 manually, automatically, or a combination of manually and automatically. In such an instance, the segmentation process would not entail applying a spline 110 to each of the two-dimensional image slices 108. Instead, the 3D statistical or generic bone model would be fitted or morphed to the shape of the femur 104 in the scanned image 108. Thus, the morphed or fitted 3D bone model would entail the 3D bone model 112 shown in FIG. 4E.

In one embodiment, the generic bone model may be a result of an analysis of the medical images (e.g., CT, MRI, X-ray, etc.) of many (e.g., thousands or tens of thousands) of actual bones with respect to size and shape, and this analysis is used to generate the generic bone model, which is a statistical average of the many actual bones. In another embodiment, a statistical model is derived which describes the statistical distribution of the population, including the variation of size, shape and appearance in the image.

In certain instances, other methods of generating patient models may be employed. For example, patient bone models or portions thereof may be generated intra-operatively via registering a bone or cartilage surface in one or more areas of the bone. Such a process may generate one or more bone surface profiles. Thus, the various methods described herein are intended to encompass three dimensional bone models generated from segmented medical images (e.g., CT, MRI) as well as intra-operative imaging methods, and others.

While the imaging and subsequent steps of the method are described in reference to a knee joint 102, the teachings in the present disclosure are equally applicable to other joints such as the hip, ankle, shoulder, wrist, and elbow, among others.

B. Preoperative Planning of Implant Selection, Positioning and Orientation of the Implant After the 3D femoral model 112 of the patient joint 102 is generated, the remaining parts of the preoperative planning may commence. For instance, the surgeon or the system may select an appropriate implant, and the implant position and orientation may be determined. These selections may determine the appropriate cuts or resections to the patient bones in order to fit the chosen implant. Such preoperative planning steps may be found in PCT/US2016/034847, filed May 27, 2016, which is hereby incorporated by reference in its entirety.

III. Surgical Procedure

After the preoperative planning steps are completed, the surgery may commence according to the plan. That is, the surgeon may use the haptic device 60 of the surgical system 100 to perform resections of the patient's bone, and the surgeon may implant an implant to restore the function to the joint. Steps of the surgical procedure may include the following.

A. Registration

Registration is the process of mapping the preoperative plan including the bone models 112 (of FIG. 4E) and the associated virtual boundaries or tool paths to the patient's physical bones so the robotic arm 60 is spatially oriented relative to the patient's physical bones in order to accurately perform the surgical procedure. The preoperative plan including the bone models 112 and associated virtual boundaries or tool paths may be stored on the computer 50 in a first coordinate system (x1, y1, z1). The navigation system 42, which tracks the movements of the robotic arm 60 via various tracker arrays (e.g., 48, 54), is also in communication with the computer 50. The navigation system 42 also tracks the patient's body via various tracker arrays 46 positioned on the tibia 10 and femur 11. In this way, the position and orientation (i.e., pose) of the robotic arm 60 and the operative bones 10, 11 are known relative to each other in a second coordinate system (x2,y2,z2) in the computer 50. The process of mapping, transforming, or registering the first coordinate system (x1, y1, z1) and the second coordinate system (x2,y2,z2) together in a common coordinate system is known as registration.

Once registered, the bone models 112 and virtual boundaries or toolpaths may be "locked" to the appropriate location on the patient's physical bone such that any movement of the patient's physical bone will cause the bone models 112 and virtual boundaries or toolpaths to move accordingly. Thus, the robot arm 60 may be constrained to operate with the virtual boundaries or along the toolpath, which is defined in the preoperative plan, and which moves with the patient's bones as they move. In this way, the robotic arm 60 is spatially aware of the pose of the patient's physical body via the registration process.

As stated previously, registration techniques include the point-based registration technique described in U.S. Pat. No. 8,010,180, and 2D/3D registration utilizing a hand-held radiographic imaging device as described in U.S. application Ser. No. 13/562,163, titled "Radiographic Imaging Device," filed Jul. 30, 2012, and hereby incorporated by reference herein in its entirety. As described in U.S. Pat. No. 8,010, 180, among others, various points on the patient's bone are contacted with a navigated probe, and the computer records the positions of the point in a point-cloud. Once a sufficient number of points are stored in the point-cloud, the data in the point-cloud may be registered to a bone model of the patient stored in the computer.

B. Registration Tools

Figure 5A:
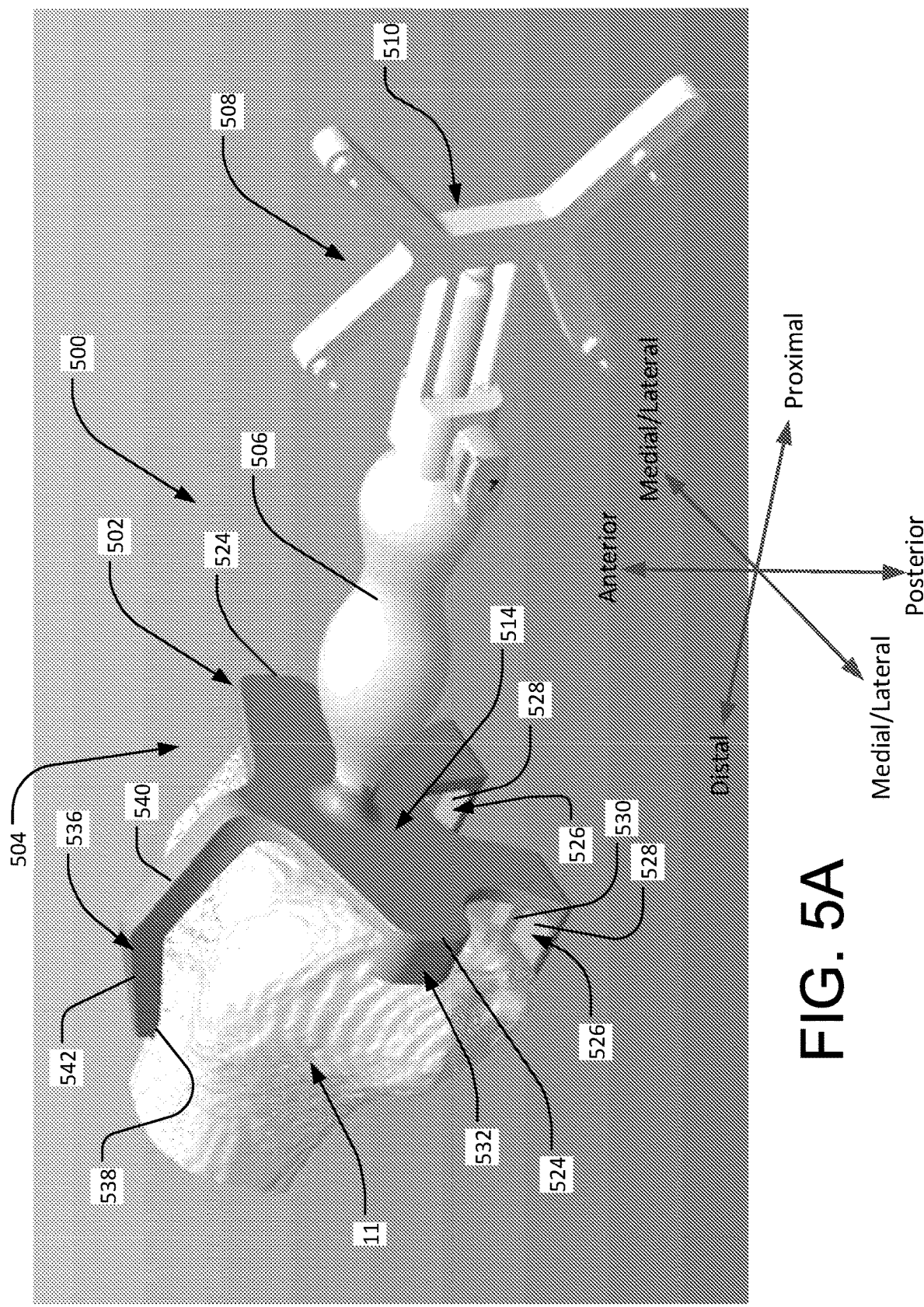
FIG. 5A is an isometric view of a registration tool positioned on a femur.

Instead of a point-based approach to registration, specific registration tools may be utilized to quickly and accurately register a patient's physical bone 11 to a bone model 112. An exemplary registration tool or probe 500 is illustrated in FIG. 5A. The registration tool 500 includes an engagement structure 502 (also known as a "bone engagement structure") at a distal end 504, a handle 506 extending proximally from engagement structure 502, and a tracker array 508 coupled to a proximal end 510 of the handle 506. The bone engagement structure 502 is non-patient-specific, meaning it is not customized for a particular patient. Stated differently, the bone engagement structure is a generic structure that can be used by many patients. The tracker array 508 may be slidably coupled to the handle 506 to facilitate removable engagement between the tracker array 508 and the handle 506. The engagement structure 502 is sized and configured to contact bone and/or cartilage surrounding a bone 11, which is at a distal end of a femur in FIG. 5A.

It is noted that the terms distal, proximal, anterior, posterior, medial, and lateral are used with reference to the registration tool 500 itself, and how it is applied to a bone 11. That is, the engagement structure 502 is advanced towards and contacts the patient bone 11; thus, it is referred to as being at the distal end 504 of the tool 500. At the other end, the tracker array 508 is positioned opposite the distal end 504 when the tool 500 is used on the bone 11; thus, the tracker array 508 is at a proximal end 510 of the tool 500. The medical terms of direction are shown in FIG. 5A as it relates to the registration tool 500. Note that in FIG. 5A, the tool 500 is applied to the distal end of the bone 11. While medical terms of direction, such as distal, proximal, anterior, posterior, medial, and lateral, are used in the description, other terms such as front, back, top, bottom, and sides may be used without limitation and without departing from the teachings of the present disclosure.

Figure 5F:
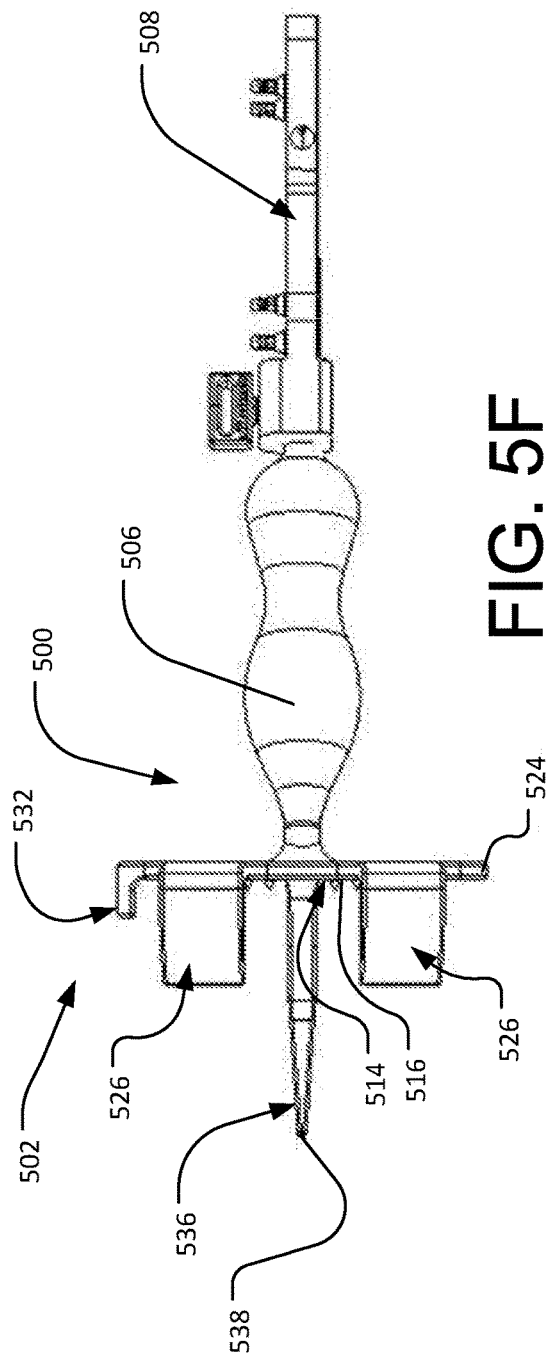
FIG. 5F is a bottom view of the registration tool.
Figure 5G:
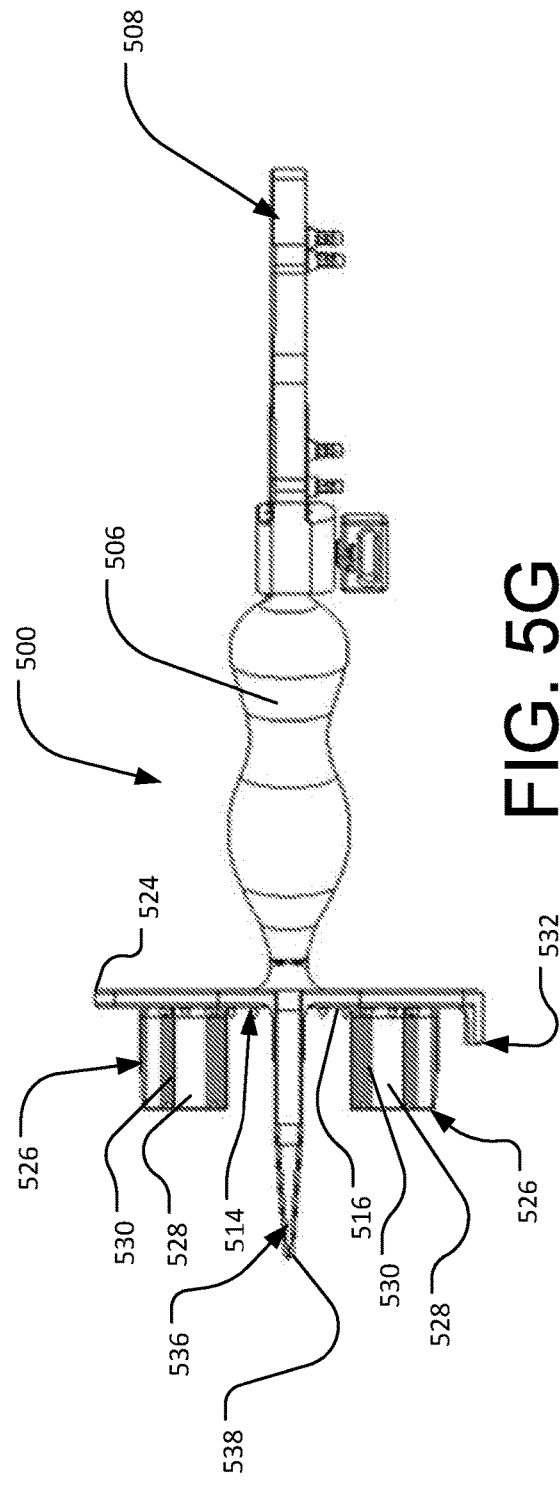
FIG. 5G is a top view of the registration tool.

Continuing on, the engagement structure 502 may include specific surfaces for engaging a femur as is illustrated in FIGS. 5B-5G. FIG. 5B is a front view of the registration tool 500. FIG. 5C is a rear view of the registration tool 500. FIG. 5D is a first side view of the registration tool 500. FIG. 5E is a second side view of the registration tool 500, the second side view being opposite the first side view. FIG. 5F is a bottom view of the registration tool 500. And FIG. 5G is a top view of the registration tool 500.

As seen in FIG. 5B, the engagement structure 502 may include a distal condyle abutment structure 514 (also referred to as "condyle abutment structure", "distal abutment structure" or "abutment structure") having a distal surface 516 including a series of spikes or blades 518 extending outward from the surface 516. When used on the knee, the spikes 518 are designed to penetrate the cartilage on the distal condyles of the bone 11 and extend to the bone surface situated beneath the cartilage. The distal surface 516 may be a planar surface sized to span across both a medial and lateral condyle of a bone 11. The distal surface 516 may include two individual abutment surfaces separated by an aperture 520 for receiving a fastener 522 that secures to a distal end of the handle 506, in the case of a releasable connection between the handle 506 and the engagement structure 502. In certain instances, the handle 506 and engagement structure 502 may be a single piece construction, as opposed to a multi-piece construction as shown in FIGS. 5A-5K.

In certain instances, there may various sizes of registration tools 500 that are sized and dimensioned to fit various bone sizes. And in certain instances, the registration tool 500 may be adjustable to fit various bone sizes.

As seen in FIGS. 5B and 5D-5G, the engagement structure 502 may include a pair of posterior condyle abutment structures 526 (also referred to as "paddles", or "posterior abutment structure") including posterior surfaces 528 that face anteriorly, each including a pair of knife edges 530 extending a length of the abutment structures 526. The posterior surfaces 528, as best seen in FIGS. 5B and 5D-5E, may be planar surfaces that are oriented generally perpendicular to the distal surface 516. The knife edges 530 are designed to cut through the cartilage on the posterior side of the condyles. In use, the registration tool 500 may be advanced towards the distal end of the femur 11 such that the knife edges 530 cut into the cartilage on the posterior condyles. It is noted that the posterior surfaces 528 each include a single knife edge 530 in FIG. 5A. In certain instances, the posterior surfaces 528 may include no knife edges, one knife edge 530, two knife edges 530, or three knife edges 530, among other numbers of knife edges 530.

In certain instances, the registration tool 500 may be modified for a partial knee arthroplasty, among other procedures, where the tool 500 may include only a single posterior condyle abutment structure 526 having a single posterior surface 528. In such an instance, the tool 500 may include a distal condyle abutment structure 514 that includes only a medial or lateral side (i.e., half the size of that shown in the figures).

As best seen in FIGS. 5A-5B and 5D-5G, the engagement structure 502 of the registration tool 500 may additionally include a medial/lateral condyle abutment structure 532 (also referred to as a "side structure" or a "side abutment structure") having a surface 534 extending distally off of an edge 524 of the distal condyle abutment structure 514. The medial/lateral facing surface 534 may be a planar surface positioned generally perpendicular to the distal facing surface 516 of the distal condyle abutment structure 514, as best seen in FIGS. 5F and 5G. The registration tool 500 may be used on either the left or right knee of a patient. That is, when the registration tool 500 is utilized on a patient's knee, the medial/lateral facing surface 534 may contact a medial side of the knee or the lateral side of the knee depending on what knee is subject to the operation. As described herein, the medial/lateral condyle abutment structure 532 may alternatively be referred to as a medial condyle abutment structure 532, a lateral condyle abutment structure 532, and/or a side condyle abutment structure 532.

As best seen in FIGS. 5A-5B and 5D-5G, the engagement structure 502 may additionally include an anterior shaft abutment structure 536 (also known as an "anterior abutment structure") having an anterior shaft facing surface 538 at a distal end thereof. The anterior shaft abutment structure 536 may include an elongated member with a proximal section 540 and a distal section 542 that are angled relative to each other by an obtuse angle that is less than one hundred eighty degrees, in certain instances. In this way, the angled nature of the anterior shaft abutment structure 536 extends up and around the anterior side of the femoral condyles without contacting them such that the only contact with the femur is by the anterior shaft facing surface 538 at the distal end thereof. And while the anterior shaft abutment structure 536 includes a single member extending from the distal condyle abutment structure 514, the anterior shaft abutment structure 536 may include two or more structures extending from the distal condyle abutment structure 514 for contacting the anterior shaft portion of the knee.

As best seen in FIGS. 5B and 5F-5G, there is only one medial/lateral condyle abutment structure 532. In this way, the registration tool 500 can accommodate various sizes of knees for registration since one side of the engagement structure 502 is open or without any distally protruding structure (i.e., medial/lateral condyle abutment structure 532).

Figure 5H:
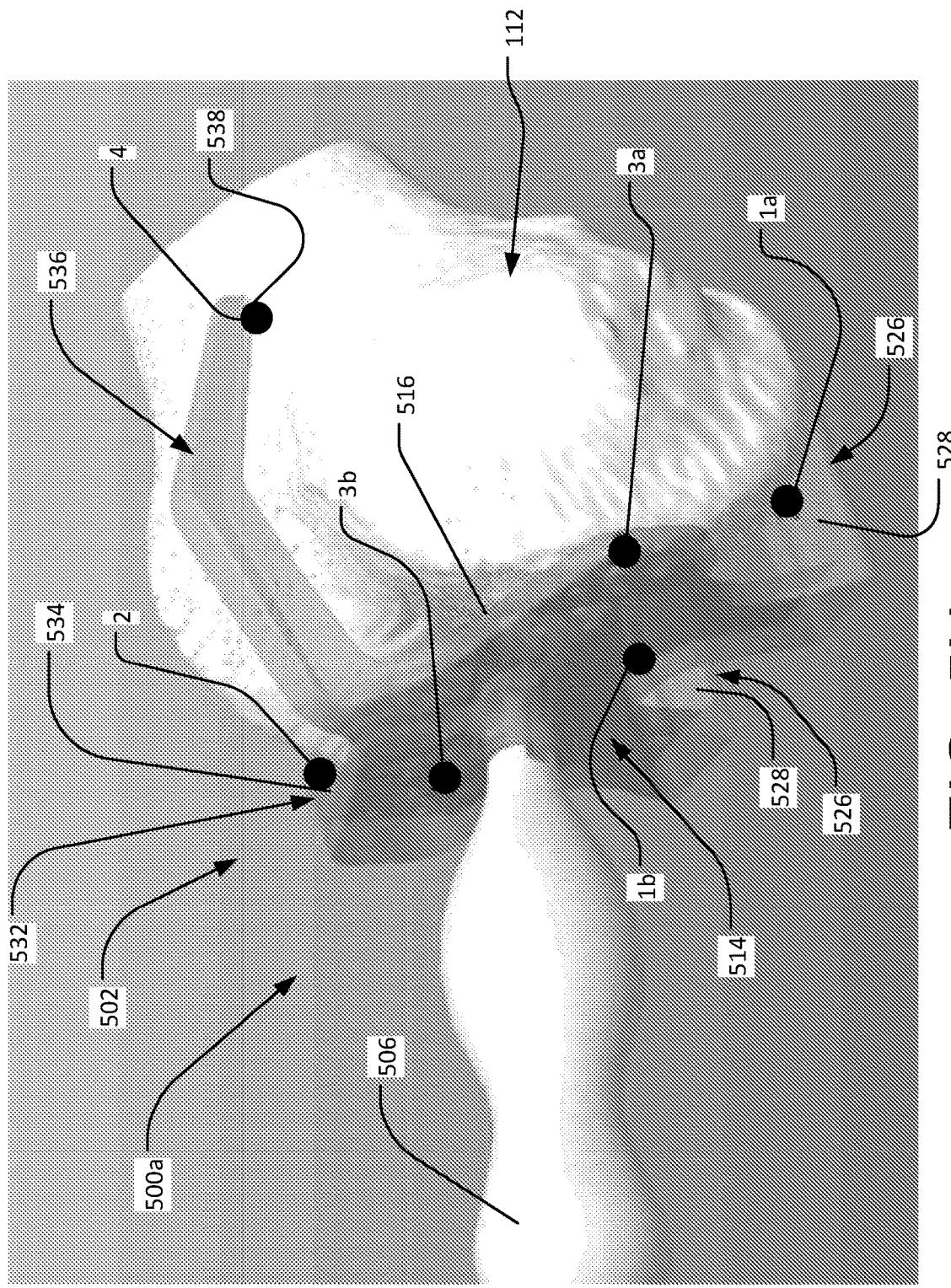
FIG. 5H is an isometric view of a registration tool model positioned relative to a femoral bone model, showing six points of contact therebetween.
Figure 6A:
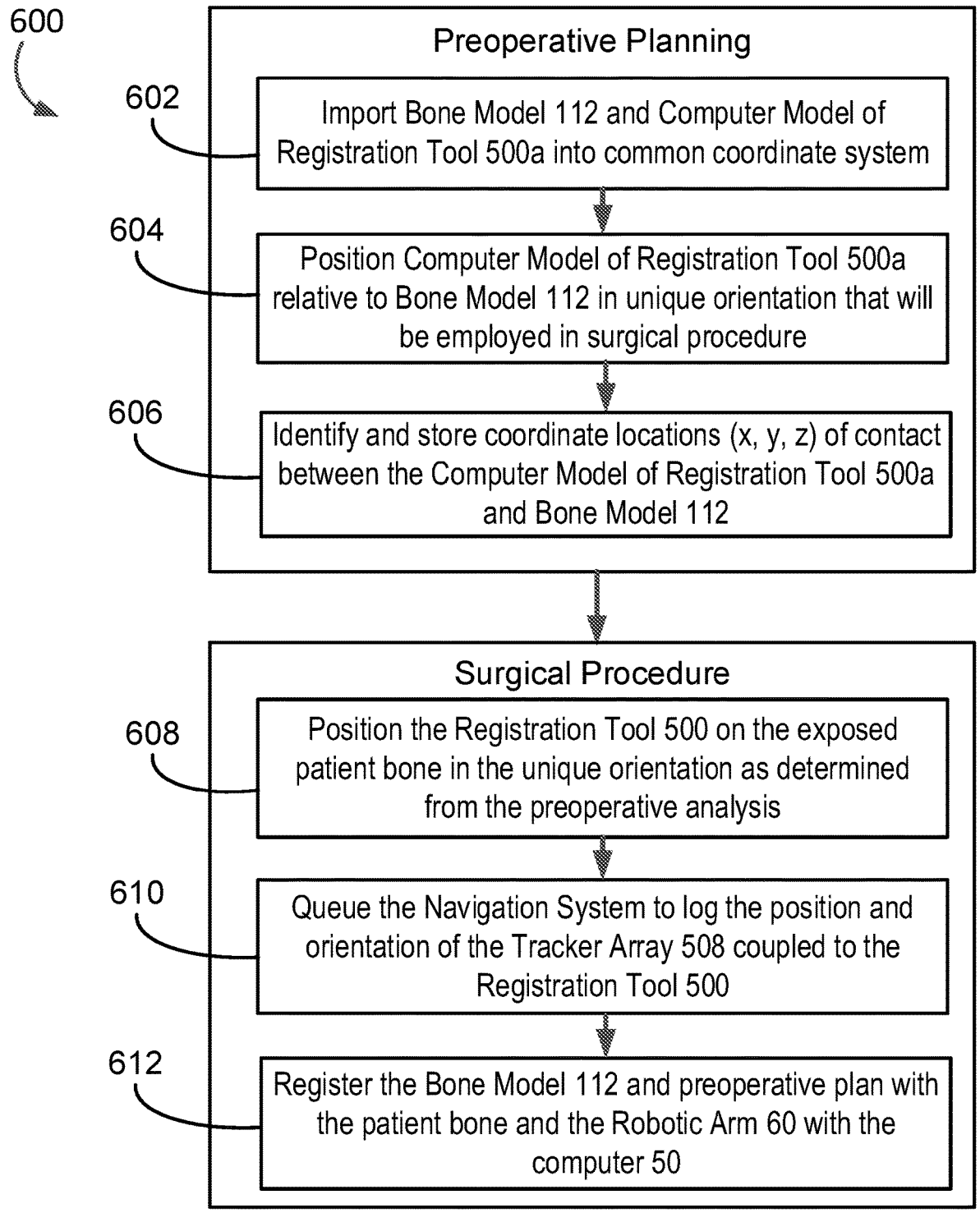
FIG. 6A is a flowchart illustrating various steps of using the registration tool in preoperative planning and during a surgical procedure.

FIG. 6A shows a flowchart of steps for using the registration tool 500 in a registration procedure of a computer assisted surgical procedure. As seen in the figure, the procedure 600 may entail the following steps. At step 602, the bone model 112 representing the patient bone and the computer model of the registration tool 500a (also referred to as a virtual registration tool 500a) may be imported or received into a common coordinate system (x, y, z) of the computer 50. This step 602, or the next step 604, may include choosing a suitable size of registration tool 500a based on a size of the bone. Next, step 604 may include positioning the computer model of the registration tool 500a (also referred to as "virtual registration tool") relative to the bone model 112 in a unique position and orientation (pose) that will be employed in the surgical procedure. This step 604 is illustrated in FIG. 5H, with the registration tool 500a, shown transparently in the figure, positioned against the bone model 112 in a unique orientation that constrains translation and rotation of the tool 500a relative to the bone model 112 in all degrees of freedom via six contact points. In the unique orientation, as seen in FIG. 5H, contact between the registration tool 500a and the bone model 112 is as follows: 1) posterior aspect of lateral condyle 1a of femur bone model 112 contacts one of the pair of posterior condyle facing surfaces 528 of the posterior condyle abutment structures 526; 2) posterior aspect of medial condyle 1b of femur bone model 112 contacts the other one of the pair of posterior condyle facing surfaces 528 of the posterior condyle abutment structures 526; 3) medial side of medial condyle 2 of femur bone model 112 contacts the surface 534 of the medial/lateral condyle abutment structure 532; 4) distal aspect of lateral condyle 3a of femur bone model 112 contacts a lateral portion of the distal facing surface 516 of the distal condyle abutment structure 514; 5) distal aspect of medial condyle 3b of femur bone model 112 contacts a medial portion of the distal facing surface 516 of the distal condyle abutment structure 514; and 6) anterior shaft 4 of femur bone model 112 contacts the anterior shaft facing surface 538 of the anterior shaft abutment structure 536. It is noted that in certain instances, there may be more or less contact points between the registration tool 500a and the bone model 112. For example, a registration tool 500a for a partial knee arthroplasty may include less points of contact between the tool 500a and the bone model 112.

When the registration tool 500a is positioned in the unique pose with six contact points contacting the femur bone model 112, the tool is "locked" relative to the bone model 112 in all six degrees of freedom such that no rotation or translation is permitted. The coordinate points for the contact points 1a, 1b, 2, 3a, 3b, and 4 on the bone model 112 can be stored by the computer 50 to be used in the registration algorithm since the physical registration tool 500 should contact the same points on the actual patient bone during the surgery.

Figure 5J:
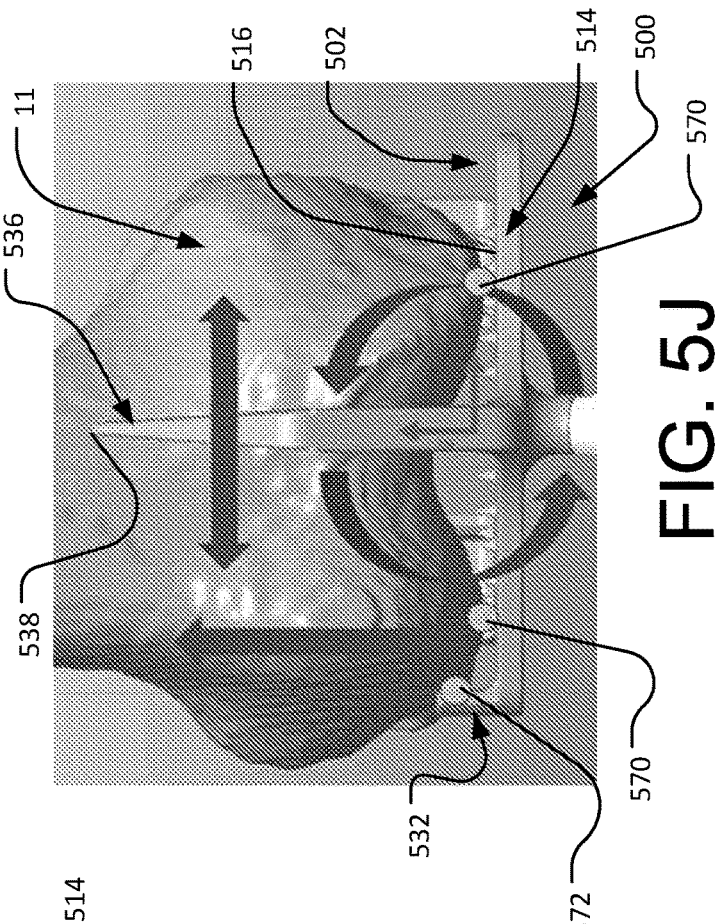
FIG. 5J is a top view of the registration tool positioned on a femur.
Figure 5I:
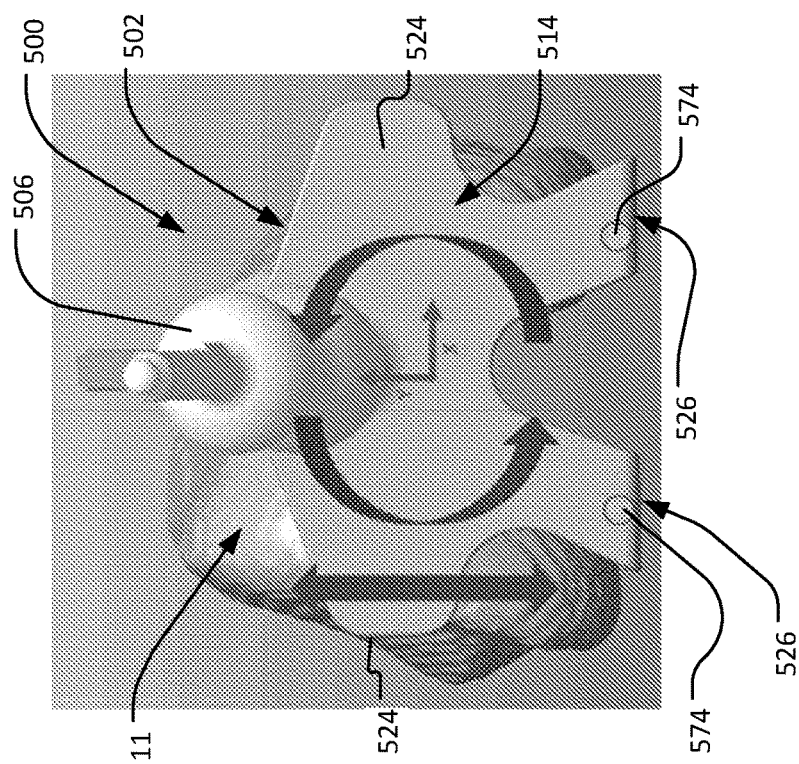
FIG. 5I is a rear view of the registration tool positioned on a femur.
Figure 5K:
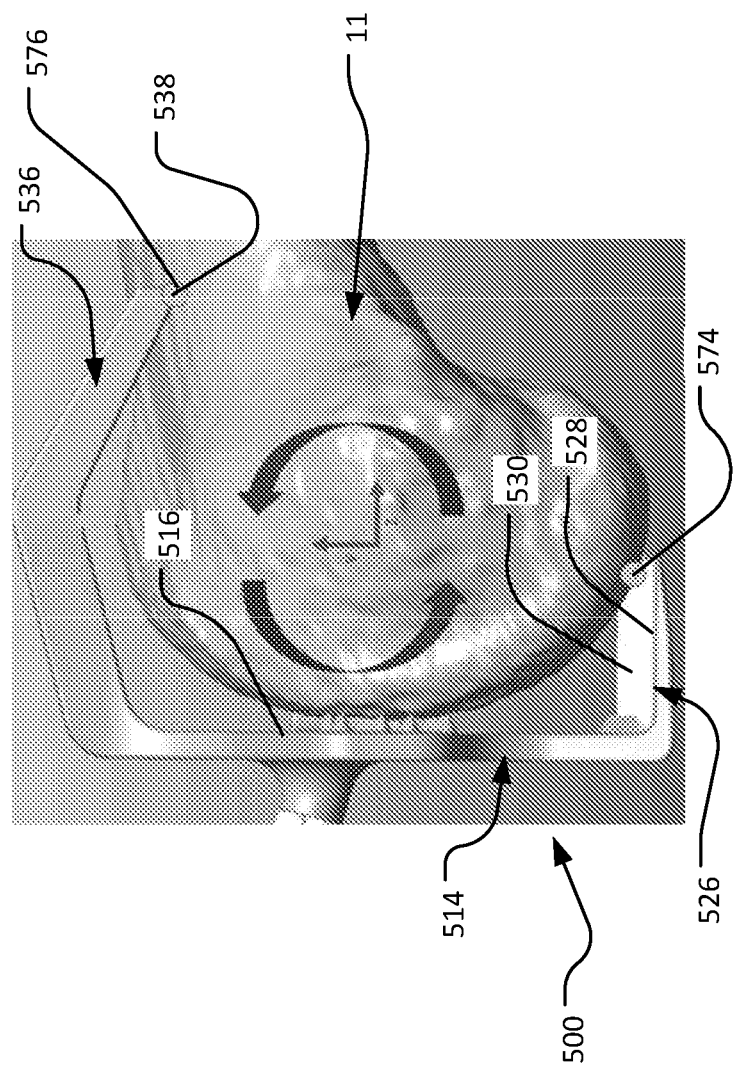
FIG. 5K is a side view of the registration tool positioned on a femur.
Figure 5M:
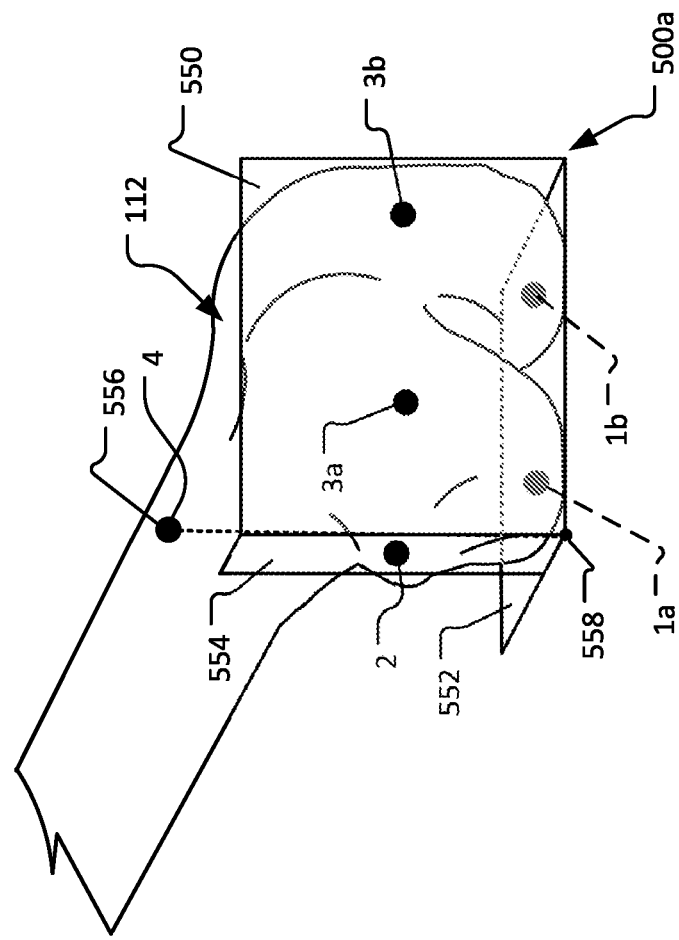
FIG. 5M is an isometric view of a femur bone model with the virtual registration tool of FIG. 5L positioned thereon.
Figure 5L:
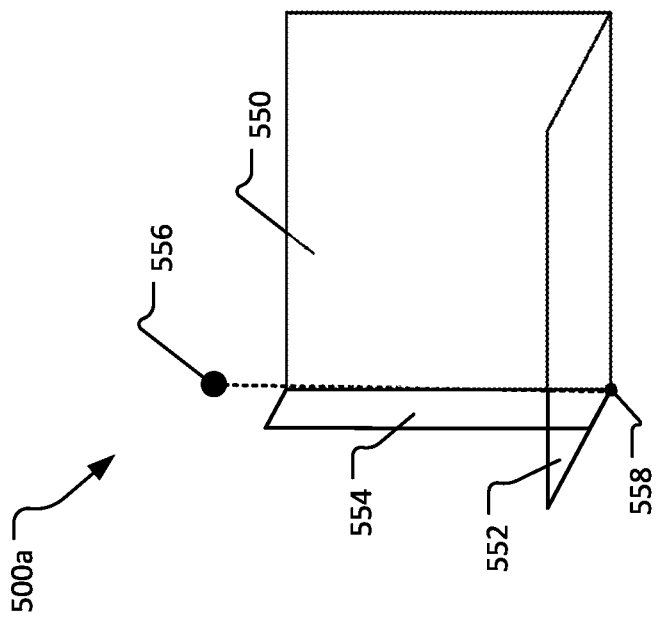
FIG. 5L is an isometric view of a virtual registration tool defined by three planes and a point.

While FIG. 5H depicts the registration tool 500a virtually as it appears physically, the registration tool 500a may, additionally or alternatively, be depicted as a trio of planes (or series of planes, plurality of planes, etc.) and a point, as illustrated in FIGS. 5L and 5M. FIG. 5L illustrates the registration tool 500a as a distal plane 550, a posterior plane 552, a medial/lateral plane 554 (or "side plane"), and an anterior point 556. As seen in FIG. 5L, the trio of planes 550, 552, 554 intersect at a single point 558, and the planes are mutually perpendicular. Stated differently, the planes 550, 552, 554 define three mutually perpendicular planes. The distal plane 550 corresponds to the distal facing surface 516 of the distal condyle abutment structure 514, as seen in FIG. 5B, among others. The posterior plane 552 corresponds to the pair of posterior condyle facing surfaces 528 of the posterior condyle abutment structures 526, as seen in FIG. 5B, among others. The side plane 554 corresponds to the medial/lateral facing surface 534 of the medial/lateral condyle abutment structure 532, as seen in FIG. 5B, among others. And the anterior point 556 corresponds to the anterior shaft facing surface 538 of the anterior shaft abutment structure 536, as seen in FIG. 5B, among others. On FIG. 5L, there is a dotted line connecting the anterior point 556 to the origin. This is merely to reference that the point is fixed relative to the origin.

It is noted that since the physical bone may be covered, at least partially, in cartilage, the distal plane 550 may actually correspond to the spikes 518 on the distal condyle abutment structure 514, and the posterior plane 552 may actually correspond to the blades 530 on the posterior condyle abutment structure 526. Certain types of imaging accurately depict cartilage, such as MRI, whereas certain types of imaging, such as CT, do not depict cartilage. Therefore, the planning of the pose of the registration tool 500a can be physically recreated during surgical registration by the spikes 518 and blades 530 cutting through the cartilage to the bone surface. Using a registration tool that does not account for the cartilage on the bone can lead to inaccuracies.

The virtual registration tool 500a may be positioned relative to the femur bone model 112, in a common coordinate system, as seen in FIG. 5M. As seen in the figure, the bone model 112 is positioned as close to the origin point or intersection point of the plane 558 as possible while not intersecting any of the planes 550, 552, 554 or the point 556. When the bone model 112 contacts the registration tool 500a at six points, the tool 500a is restrained from translation and rotation. In the pose shown in FIG. 5M, the contact between the registration tool 500a and the bone model 112 is as follows: 1) posterior aspect of lateral condyle 1a of femur bone model 112 contacts one side of the posterior plane 552; 2) posterior aspect of medial condyle 1b of femur bone model 112 contacts another side of the posterior plane 552; 3) lateral side of lateral condyle 2 of femur bone model 112 contacts the side plane 554; 4) distal aspect of lateral condyle 3a of femur bone model 112 contacts one side of the distal plane 550; 5) distal aspect of medial condyle 3b of femur bone model 112 contacts another side of the distal plane 550; and 6) anterior shaft 4 of femur bone model 112 contacts the anterior point 556.

Turning back to the steps 600 of FIG. 6A, step 606 may include identifying and storing the coordinate locations of contact points between the computer model of the registration tool 500a and the bone model 112. Additionally or alternatively, the coordinate system of the virtual registration tool 500a may be stored which will allow projection of the coordinate points associated with contact between the virtual tool 500 and the bone model 112. The location and orientation of the registration tool 500a relative to the bone model 112 may be stored.

It is noted that if the virtual registration tool 500a does not "fit" the femur bone model 112, a different size of virtual registration tool 500a may be selected and then "fit" onto the bone model 112. The size of the virtual registration tool 500a that best-fits the virtual bone model 112 may then be stored in the system, and a corresponding physical registration tool 500 of the same size may be used during the actual surgery.

Then, during the actual surgery on the patient, the registration tool 500 may be provided to the surgeon. When the surgeon is ready to register the robotic arm 60 to the patient bone, the surgeon may position the registration tool 500 on the exposed patient bone in the unique orientation as determined in the preoperative analysis, at step 608 of FIG. 6A.

FIG. 6B is a flowchart illustrating exemplary steps of step 608 of FIG. 6A. As seen in FIG. 6B, the step 608 may include, at step 608*a*, contacting the pair of posterior condyle facing surfaces 528 of the posterior condyle abutment structures 526 with a posterior aspect of femoral condyles 1*a* such that the blades 530 cut through cartilage and contact bone. At step 608*b*, the surgeon may advance the tool 500 proximally relative to the distal femur condyles until the distal facing surface 516 of the distal condyle abutment structure 514 contacts the distal aspect of the femoral condyles 3*a*, 3*b*. At step 608*c*, the surgeon may move the tool 500 medially or laterally (depending on the left or right knee at issue) until the medial/lateral facing surface 534 of the medial/lateral condyle abutment structure 532 contacts the medial or lateral aspect of the knee 2. And at step 608*d*, the surgeon may rotate tool 500 about a medial/lateral axis (transepicondylar axis) until the anterior shaft facing surface 538 of the anterior shaft abutment structure 536 contacts the anterior shaft 4 of the femur. It is noted that the order of operation of the steps 608*a*-608*d* may be done in the order shown in FIG. 6B or a different order without limitation. As one example, Step 608*c* may occur prior to step 608*b*.

FIGS. SI through 5K illustrate the registration tool 500 employed on a femur 11 during surgical registration, as detailed in the steps 608 in FIG. 6B. As seen in FIG. 5I, which is a distal view of the femur 11 with the registration tool 500 positioned thereon, during the positioning step 608, the posterior contact points 574 on the patient femur 11 contact the pair of posterior condyle facing surfaces 528 of the posterior condyle abutment structures 526. Such contact prevents anterior-posterior translation, and axial rotation of the registration tool 500 relative to the bone 11 as indicated by the arrows in FIG. 5I As seen in FIG. 5J, which is an anterior view of the femur 11 with the registration tool 500 positioned thereon, during the positioning step 608, the distal contact points 570 on the patient femur 11 contact the distal facing surface 516 of the distal condyle abutment structure 514. Such contact prevents distal-proximal translation, and rotation about an anterior-posterior axis. Also, as seen in FIG. 5J, the medial side of medial condyle 572 of femur 11 contacts the surface 534 of the medial/lateral condyle abutment structure 532, and prevents medial-lateral translation of the registration tool 500 relative to the femur 11. As seen in FIG. 5K, which is a lateral view of the femur 11 with the registration tool 500 positioned thereon, during the positioning step 608, contact between the posterior contact points 574 on the pair of posterior condyle facing surfaces 528 of the posterior condyle abutment structures 526 and contact between the anterior shaft 576 of femur 11 and the anterior shaft facing surface 538 of the anterior shaft abutment structure 536 prevents rotation about a medial-lateral axis.

Thus, as seen in FIGS. 5I-5K, translation along the anterior-posterior plane, distal-proximal plane, and medial-lateral plane is constrained via the registration tool 500, and rotation about the axial (distal-proximal) axis, anterior-posterior axis, and medial-lateral axis is also constrained via the registration tool 500.

Once the registration tool 500 is positioned in the unique orientation on the patient bone, the surgeon may queue the navigation system 42 to store the position and orientation of the tracker array 508 that is coupled to the handle 506 of the registration tool 500, at step 610 of FIG. 6A. Then, the bone model 112 and the preoperative plan may be registered with the patient bone 11 and the robotic arm 60, at step 612. Since the navigation system 42 is tracking the pose of the registration tool 500, once the registration tool 500 is positioned in the unique orientation on the patient bone 11 and the orientation is stored in the computer 50, the registration process may map the bone model 112 into the position and orientation of the actual femur 11 (or vice versa) such that the robotic arm 60 is spatially oriented relative to the actual femur 11 as represented by the bone model 112 in the coordinate system.

While the registration tool 500 is shown as a single piece, non-adjustable tool, the registration tool 500 may be a multi-piece construction, and may be adjustable. In certain instances, any of the pair of posterior condyle abutment structures 526, medial/lateral condyle abutment structure 532, and the anterior shaft abutment structure 536 may be adjustable relative to the distal condyle abutment structure 514. In certain instances, the pair of posterior condyle abutment structures 526 may be adjustable in one or more of the anterior-posterior direction, distal-proximal direction, and the medial-lateral direction. In certain instances, the medial/lateral condyle abutment structure 532 may be adjustable in one or more of the anterior-posterior direction, distal-proximal direction, and the medial-lateral direction. In certain instances, the anterior shaft abutment structure 536 may be adjustable in one or more of the anterior-posterior direction, distal-proximal direction, and the medial-lateral direction. Various mechanisms may be included to facilitate adjusting the parts of the tool 500. For example, the registration tool 500 may include threaded members with thumbscrews that adjust the various structures of the tool 500.

FIGS. 7A-7C illustrate a registration tool 700 for use on a tibia 10. More particularly, FIG. 7A is a medial view of a tibia 10 with the registration tool 700 positioned thereon. FIG. 7B is an anterior view of the tibia 10 with the registration tool 700 positioned thereon. FIG. 7C is a distal view of the tibia 10 with the registration tool 700 positioned thereon. As seen in the figures, the tibial registration tool 700 includes an engagement structure 702 having an aperture 704 on its proximal side for receiving a shaft of a handle (not shown) or for receiving a navigated probe therein for registration purposes. In certain instances, the registration tool 700 may be modified for a partial knee arthroplasty procedure, among other procedures. In such an instance, the registration tool 700 may include a single plateau projecting structure 706 or 712.

The engagement structure 702 may include a lateral plateau projecting structure 706 having two pins 708*a* and 708*b* extending downward therefrom for contacting a lateral tibial plateau surface 710*a*, 710*b*, a medial plateau projecting structure 712 having two pins 714*a* and 714*b* extending downward therefrom for contacting a medial tibial plateau surface 716*a*, 716*b*, an anterior shaft abutment structure 718 having spikes 720 positioned thereon for contacting an anterior side 722 of the tibia 10 near the tibial tuberosity, and a medial projecting structure 724 having a laterally facing surface 726 for contacting a medial aspect 728 of the tibia 10. The registration tool 700 may include additional structures to contact additional parts of the anatomy, such as for example an anterior shaft abutment structure that extends distally to contact the anterior tibial shaft.

Figure 8:
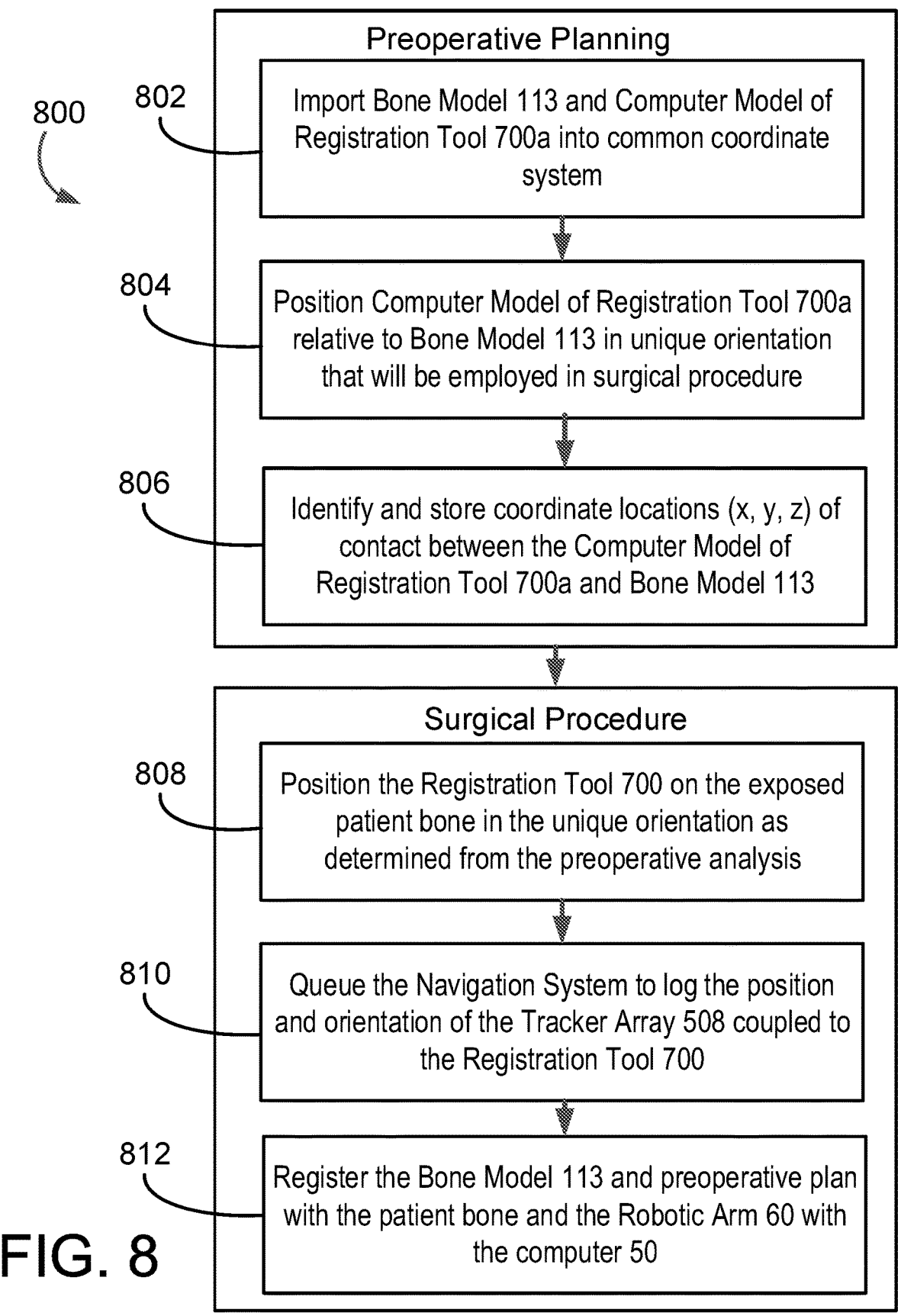
FIG. 8 is a flowchart illustrating various steps of using the tibial registration tool in preoperative planning and during a surgical procedure.

FIG. 8 shows a flowchart of steps for using the registration tool 700 in a registration procedure of a computer assisted surgical procedure. As seen in the figure, the procedure 800 may entail the following steps. At step 802, the tibial bone model 113 representing the patient bone and the computer model of the registration tool 700*a* may be imported into a common coordinate system (x, y, z) of the computer 50. This step 802, or the next step 804, may include choosing a suitable size of registration tool 700*a* based on a size of the bone. Next, step 804 may include positioning the computer model of the registration tool 700*a* relative to the bone model 113 in a unique orientation that will be employed in the surgical procedure. The unique orientation constrains translation and rotation of the tool 700*a* relative to the bone model 113 in all degrees of freedom via six contact points.

When the registration tool 700*a* is positioned in the unique position with six contact points contacting the tibial bone model 113, the tool is "locked" relative to the bone model 113 in all six degrees of freedom such that no rotation or translation is permitted. The coordinate points for the contact points 710*a*, 710*b*, 716*a*, 716*b*, 722, 728 on the bone model 113 can be stored by the computer 50 to be used in the registration algorithm since the physical registration tool 700 should contact the same points on the actual patient bone during the surgery. Turning back to the steps 800 of FIG. 8, step 806 may include identifying and storing the coordinate locations of contact points between the computer model of the registration tool 700*a* and the bone model 113.

Then, during the actual surgery on the patient, the registration tool 700 may be provided to the surgeon. When the surgeon is ready to register the robotic arm 60 to the patient bone, the surgeon may position the registration tool 700 on the exposed patient bone in the unique orientation as determined in the preoperative analysis, at step 808 of FIG. 8.

In the unique orientation, as seen in FIGS. 7A-7C, contact between the registration tool 700 and the tibia 11 is as follows: 1) a posterior pin 708*a* of the lateral plateau projecting structure 706 contacts a posterior point 710*a* on the lateral tibial plateau surface; 2) an anterior pin 708*b* of the lateral plateau projecting structure 706 contacts an anterior point 710*b* on the lateral tibial plateau surface; 3) a posterior pin 714*a* on the medial plateau projecting structure 712 contacts a posterior point 716*a* on the medial tibial plateau surface; 4) an anterior pin 714*b* on the medial plateau projecting structure 712 contacts an anterior point 716*b* on the medial tibial plateau surface; 5) the spikes 720 on the anterior shaft abutment structure 718 contacts the anterior side 722 of the tibia 10; and 6) the laterally facing surface 726 of the medial projecting structure 724 contacts a medial aspect 728 of the tibia 10.

As seen in FIG. 7A, contact between the tibia 10 and the lateral plateau projecting structure 706, the medial plateau projecting structure 712, and the anterior shaft abutment structure 718 limit rotation about a medial-lateral axis, and limit translation in an anterior-posterior direction. As seen in FIG. 7B, contact between the tibia 10 and the lateral plateau projecting structure 706, the medial plateau projecting structure 712, and the medial projecting structure 724 limits rotation about an anterior-posterior axis, limits translation in a medial-lateral direction, and limits translation in a distal-proximal direction. And as seen in FIG. 7C, contact between the tibia 10 and the anterior shaft abutment structure 718, and the medial projecting structure 724 limits rotation about a distal-proximal axis.

Once the registration tool 700 is positioned in the unique orientation on the patient bone, the surgeon may queue the navigation system 42 to store the position and orientation of the tracker array (e.g., on a navigated probe that is in contact with the aperture 704), at step 810 of FIG. 8. Then, the bone model 112 and the preoperative plan may be registered with the patient bone 11 and the robotic arm 60, at step 812. Since the navigation system 42 is tracking the pose of the registration tool 700 or the navigated probe in contact with the tool 700, once the registration tool 700 is positioned in the unique orientation on the patient bone 11 and the orientation is stored in the computer 50, the registration process may map the bone model 113 into the position and orientation of the actual tibia 10 (or vice versa) such that the robotic arm 60 is spatially oriented relative to the actual tibia 10 as represented by the bone model 113 in the coordinate system.

While the registration tool 700 in FIGS. 7A-7C shows a single piece, non-adjustable tool, the registration tool 700 may be a multi-piece construction, and may be adjustable. In certain instances, any of the lateral plateau projecting structure 706, the medial plateau projecting structure 712, and the medial projecting structure 724 may be adjustable relative to the anterior shaft abutment structure 718. In certain instances, the lateral plateau projecting structure 706 may be adjustable in one or more of the anterior-posterior direction, distal-proximal direction, and the medial-lateral direction. In certain instances, the medial plateau projecting structure 712 may be adjustable in one or more of the anterior-posterior direction, distal-proximal direction, and the medial-lateral direction. In certain instances, the medial projecting structure 724 may be adjustable in one or more of the anterior-posterior direction, distal-proximal direction, and the medial-lateral direction. Various mechanisms may be included to facilitate adjusting the parts of the tool 700. For example, the registration tool 700 may include threaded members with thumb-screws that adjust the various structures 706, 712, 724 of the tool 700.

Figure 9A:
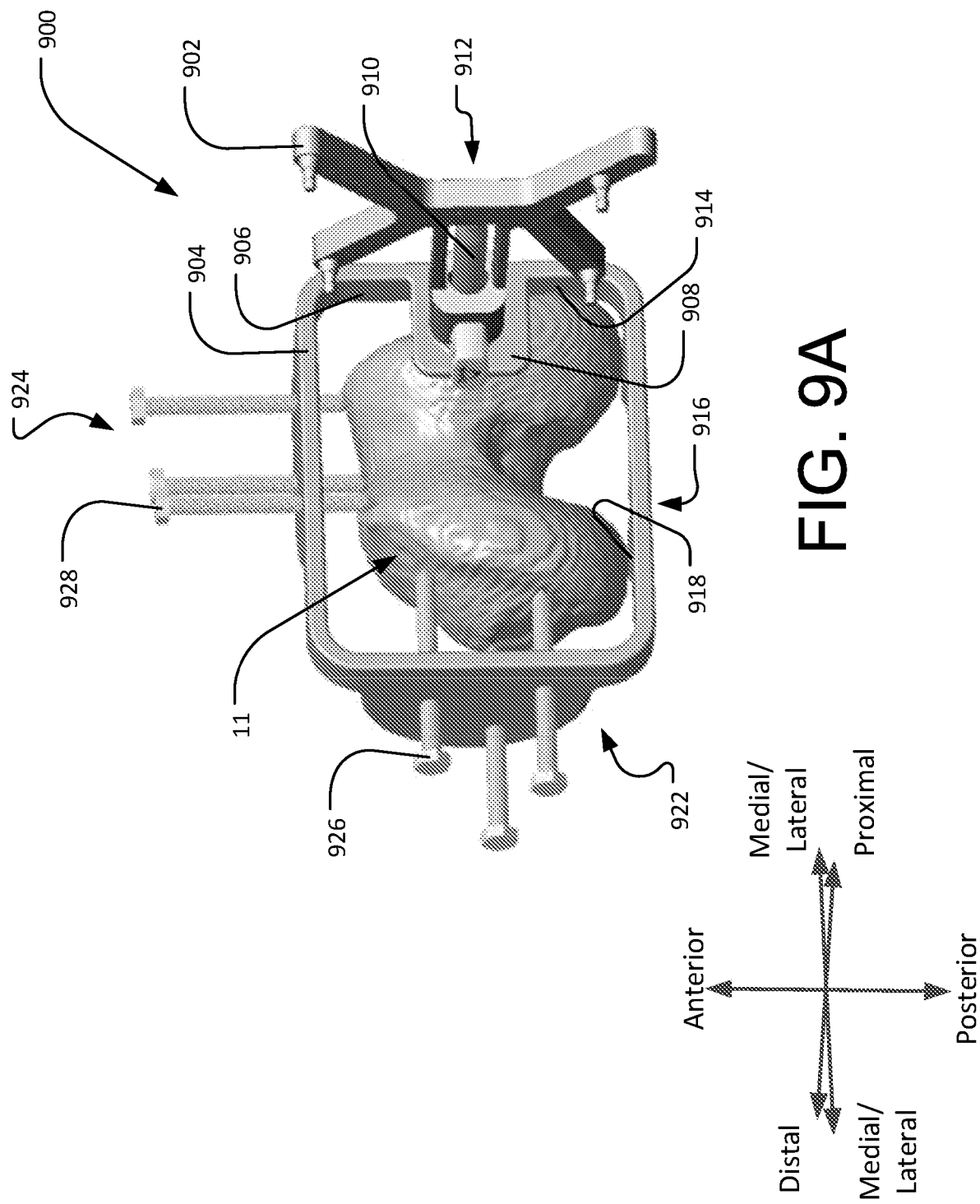
FIG. 9A is an isometric view of a registration tool positioned on a femur.
Figure 9C:
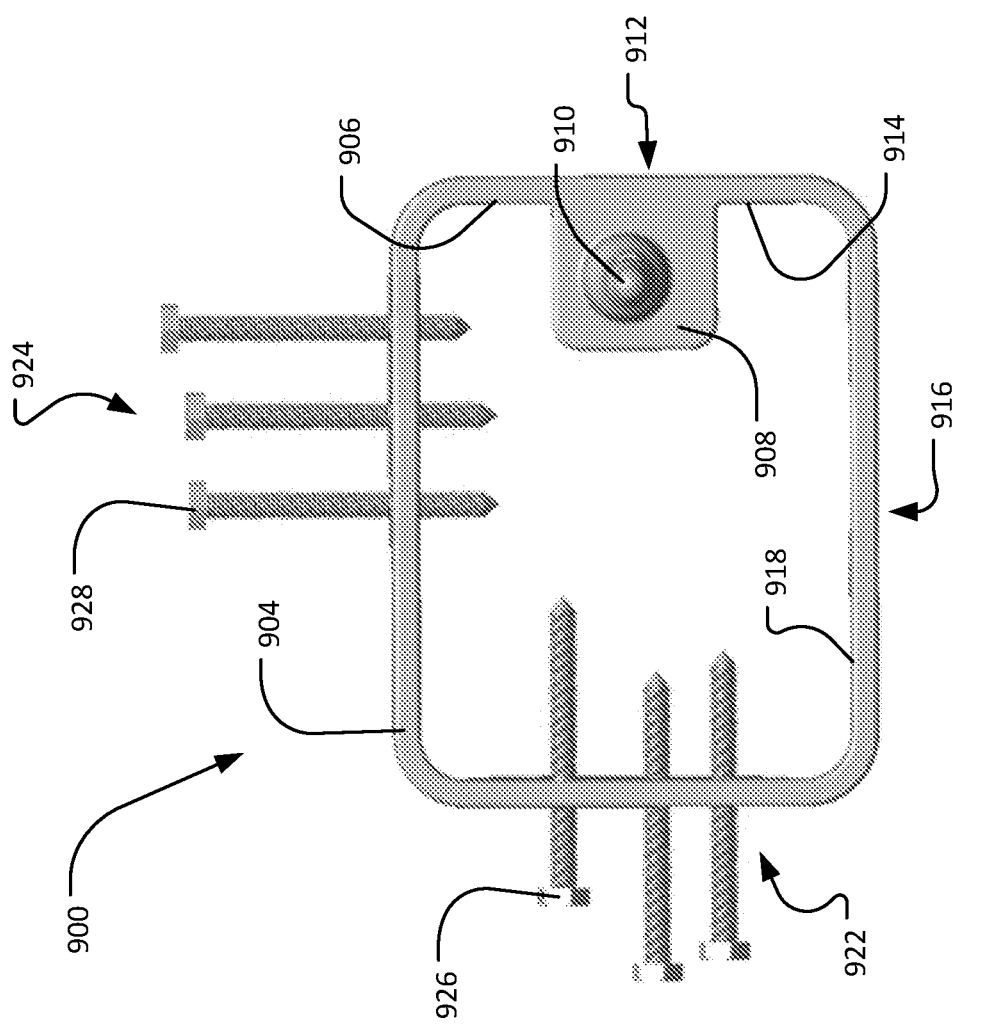
FIG. 9C is a front view of the registration tool.
Figure 9D:
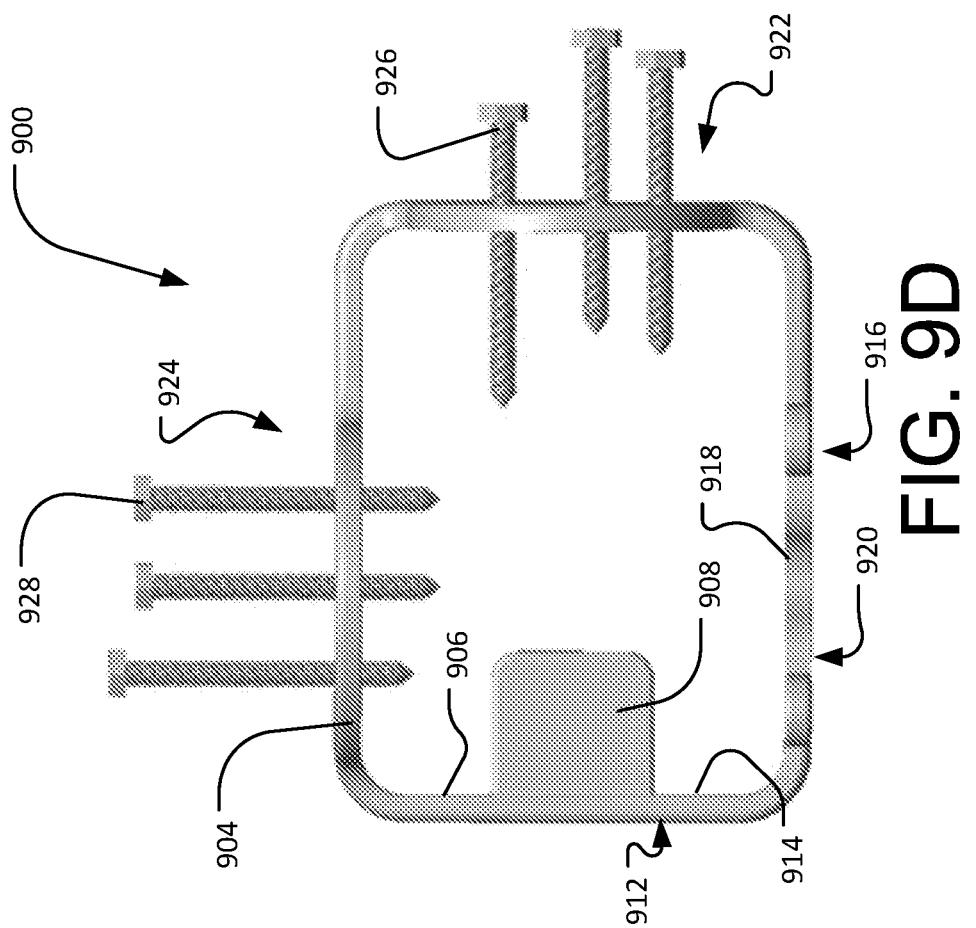
FIG. 9D is a rear view of the registration tool.

FIGS. 9A-9G illustrate a registration tool 900. FIG. 9A illustrates a front isometric view of the registration tool 900 positioned on a femur 11 with tracker array 902 coupled with the registration tool 900. FIG. 9B illustrates a rear isometric view of the registration tool 900. FIG. 9C illustrates a front view of the registration tool 900. FIG. 9D illustrates a rear view of the registration tool 900. FIGS. 9E-9G are, respectively, front, side, and top views of the registration tool 900 (in phantom) positioned on the femur 11.

The registration tool 900 of FIGS. 9A-9G includes a rectangular frame 904 having an inward facing surface 906. The frame 904 may include an inwardly extending distal condyle abutment surface 908, which may be a planar surface. The distal condyle abutment surface 908 may include a projection 910 extending proximally for coupling with the tracker array 902. The distal condyle abutment surface 908 may be positioned on a medial/lateral section 912 section of the frame 904. And as seen in FIG. 9A, the distal condyle abutment surface 908 may contact a distal aspect of the medial or lateral condyle.

The medial/lateral section 912 may also include an inward facing planar surface 914 for abutting either a medial or a lateral side of a bone 11. Adjacent the medial/lateral section 912 is a posterior condyle abutment section 916 having a planar surface 918 and a pair of posterior condyle projections 920 extending distally away from the frame 904. The posterior condyle projections 920 contact the posterior aspect of the condyles of the femur 11, as seen in FIG. 9A. Thus, as illustrated in FIG. 9A, the femur 11 may contact the registration tool as follows: 1) a distal aspect of either the medial or lateral femoral condyle contacts the distal condyle abutment surface 908; 2) either the medial or lateral side of the femoral condyle contacts the inward facing planar surface 914 of the medial/lateral section 912; 3) and the posterior condyles of the femur 11 contact the pair of posterior condyle projections 920.

The rectangular frame 904 may also include an adjustable medial/lateral section 922 opposite the medial/lateral section 912, and an adjustable anterior section 924. The medial/lateral section 922 may include three adjustable members 926 (e.g., threaded thumb-screws) extending inward from a distally extending portion of the frame 904. Similarly, the adjustable anterior section 924 may include three adjustable members 928 (e.g., threaded thumb-screws) extending inward from a distally extending portion of the frame 904. It is noted that the adjustable members 926, 928 are not collinear on the frame 904, and are not coplanar with each other. Rather, the adjustable members 926, 928 are arranged in a scattered manner on the distally extending portions of the frame 904. In this way, rotation is restrained because the adjustable members form a larger surface area of contact than would be if the adjustable members were coplanar with each other.

The three adjustable members 926 on the medial/lateral section 922 may be adjusted to contact the side (e.g., medial or lateral) of the femur 11 in a unique position, and the three adjustable members 928 on the adjustable anterior section 924 may be adjusted to contact the anterior side of the femur in a unique position. While the tool 900 is shown with three adjustable members 926 and 928 on the medial/lateral section 922 and anterior section 924, respectively, the tool 900 may include more or less adjustable members in certain instances.

It is noted that the terms distal, proximal, anterior, posterior, medial, and lateral are used with reference to the registration tool 900 itself, and how it is applied to a bone 11. That is, the rectangular frame 904 is fitted over the distal portion of the patient bone 11. At the other end of the tool 900 is the tracker array 902. The medical terms of direction are shown in FIG. 9A as it relates to the registration tool 900 in that particular figure. While medical terms of direction, such as distal, proximal, anterior, posterior, medial, and lateral, are used in the description, other terms such as front, back, top, bottom, and sides may be used without limitation and without departing from the teachings of the present disclosure.

Figure 10:
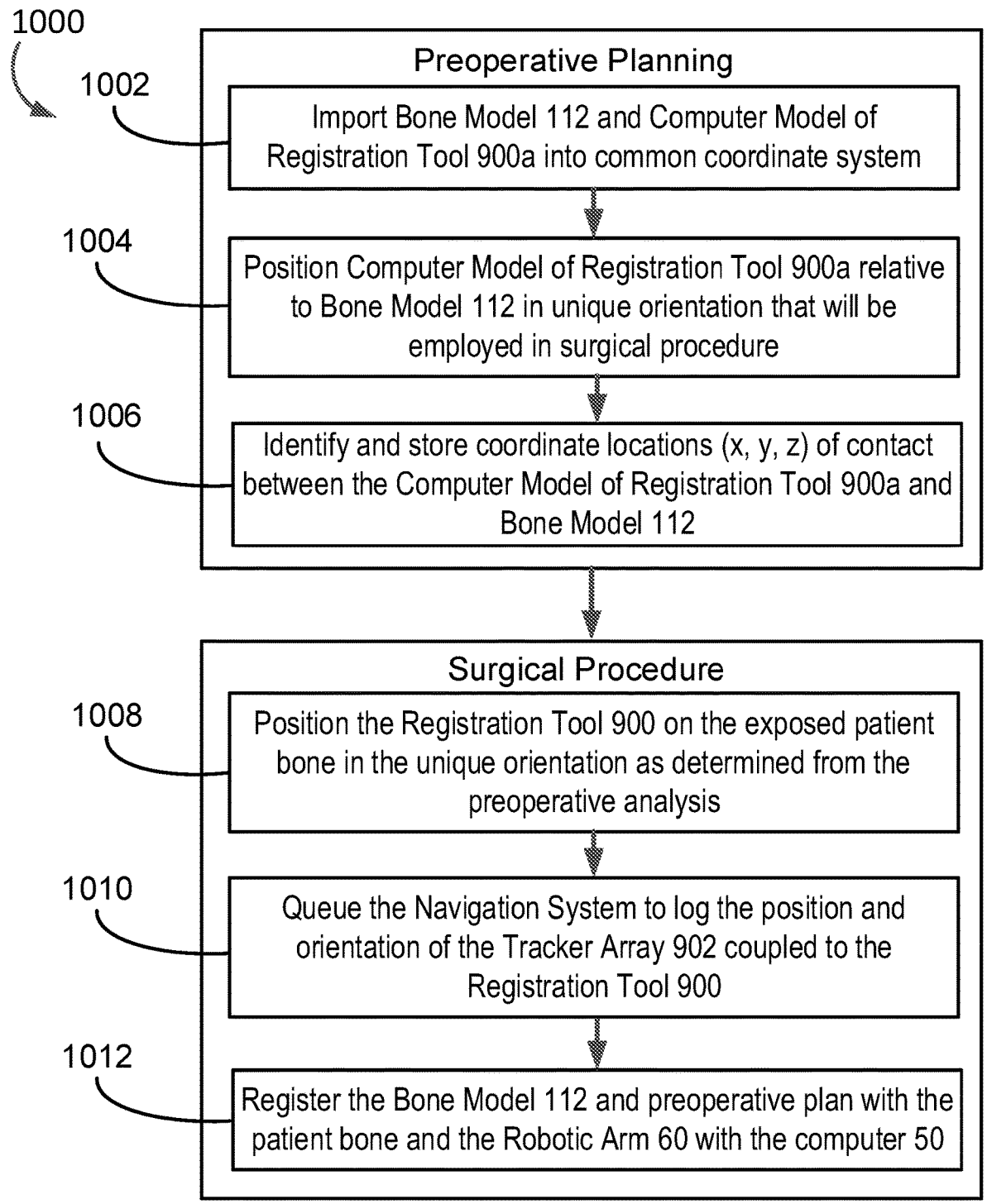
FIG. 10 is a flowchart illustrating various steps of using the registration tool in preoperative planning and during a surgical procedure.

FIG. 10 shows a flowchart of steps for using the registration tool 900 in a registration procedure of a computer assisted surgical procedure. As seen in the figure, the procedure 1000 may entail the following steps. At step 1002, the bone model 112 representing the patient bone and the computer model of the registration tool 1000a may be imported into a common coordinate system (x, y, z) of the computer 50. This step 1002, or the next step 1004, may include choosing a suitable size of registration tool 1000a based on a size of the bone. Next, step 1004 may include positioning the computer model of the registration tool 900a relative to the bone model 112 in a unique orientation that will be employed in the surgical procedure. This step 1004 is illustrated in FIGS. 9E-9G, with the registration tool 900a positioned against the bone model 112 in a unique orientation that constrains translation and rotation of the tool 900a relative to the bone model 112 in all degrees of freedom via contact with the adjustable members 926, 928, the condyle projections 920, the distal condyle abutment surface 908, and the inward facing planar surface 914 of the medial/lateral section 912.

When the registration tool 900a is positioned in the unique position with the contact points contacting the femur bone model 112, the tool is "locked" relative to the bone model 112 in six degrees of freedom such that no rotation or translation is permitted. The coordinate points for the contact points on the bone model 112 can be stored by the computer 50 to be used in the registration algorithm since the physical registration tool 900 should contact the same points on the actual patient bone during the surgery. Turning back to the steps 1000 of FIG. 10, step 1006 may include identifying and storing the coordinate locations of contact points between the computer model of the registration tool 900a and the bone model 112.

Then, during the actual surgery on the patient, the registration tool 900 may be provided to the surgeon. When the surgeon is ready to register the robotic arm 60 to the patient bone, the surgeon may position the registration tool 900 on the exposed patient bone in the unique orientation as determined in the preoperative analysis, at step 1008 of FIG. 6.

Once the registration tool 900 is positioned in the unique orientation on the patient bone, the surgeon may queue the navigation system 42 to store the position and orientation of the tracker array 902, at step 1010 of FIG. 10. Then, the bone model 112 and the preoperative plan may be registered with the patient bone 11 and the robotic arm 60, at step 1012. Since the navigation system 42 is tracking the pose of the registration tool 900, once the registration tool 900 is positioned in the unique orientation on the patient bone 11 and the orientation is stored in the computer 50, the registration process may map the bone model 112 into the position and orientation of the femur 11 (or vice versa) such that the robotic arm 60 is spatially oriented relative to the actual femur 11 as represented by the bone model 112 in the coordinate system.

The adjustable members 926, 928 of the registration tool 900 may be adjusted manually or under power to contact the patient's bone. A pre-determined amount of adjustment could be provided from a computer of the system. And the computer may sense when contact is made with the bone and stop advancement of the adjustable members 926, 928. The tool 900 may additionally include a feature to stop advancement of the adjustable members 926, 928 when a certain force is reached so as to prevent overtightening of the members 926, 928 into the bone.

FIGS. 11A-11C illustrate a registration tool 1100 for use on a femoral head 1102. More particularly, FIG. 11A is a back view of the registration tool 1100 positioned on the femoral head 1102, FIG. 11B is a side view of the registration tool 1100 positioned on the femoral head 1102, and FIG. 11C is a top view of the registration tool 1100 positioned on the femoral head 1102.

As seen in the figures, the registration tool 1100 may include a proximal structure 1104 for contacting a most proximal portion of the femoral head 1102. Four members 1106, 1108, 1110, and 1112 may extend from the proximal structure 1104 and are sized and dimensioned to fit at least partially around the femoral head 1102 in a unique orientation. A pair of superior members 1106, 1108 are positioned to contact a superior aspect of the femoral neck 1114. A side member 1110 is positioned to contact either an anterior or posterior aspect of the femoral neck 1114 depending on which femur (left or right) the tool 1100 is used on. And an inferior member 1112 is positioned to contact an inferior aspect of the femoral head 1102 near the transition to the femoral neck 1114.

FIGS. 12A-12C illustrate a registration tool 1200 for use on an acetabulum 1202. More particularly, FIG. 12A is back view of the registration tool 1200 positioned in the acetabulum 1202, FIG. 12B is top view of the registration tool 1200 positioned in the acetabulum 1202, and FIG. 12C is side view of the registration tool 1200 positioned in the acetabulum 1202.

The registration tool 1200 of FIGS. 12A-12C may include a central structure 1204 with a plurality of members or fingers 1206 extending from the central structure 1204. As seen in the figures, there are five fingers 1206 extending from the central structure 1204. The central structure 1204 and the fingers 1206 are positioned to fit within the acetabulum 1202 and dimensioned to contact points on the articular surface, acetabular fossa, acetabular notch, and/or the acetabular rim/margin in a unique orientation.

The registration tools 1100, 1200 of FIGS. 11A-12C may be used similarly as the femoral and tibial registration tools described previously.

IV. Exemplary Computing System

Figure 13:
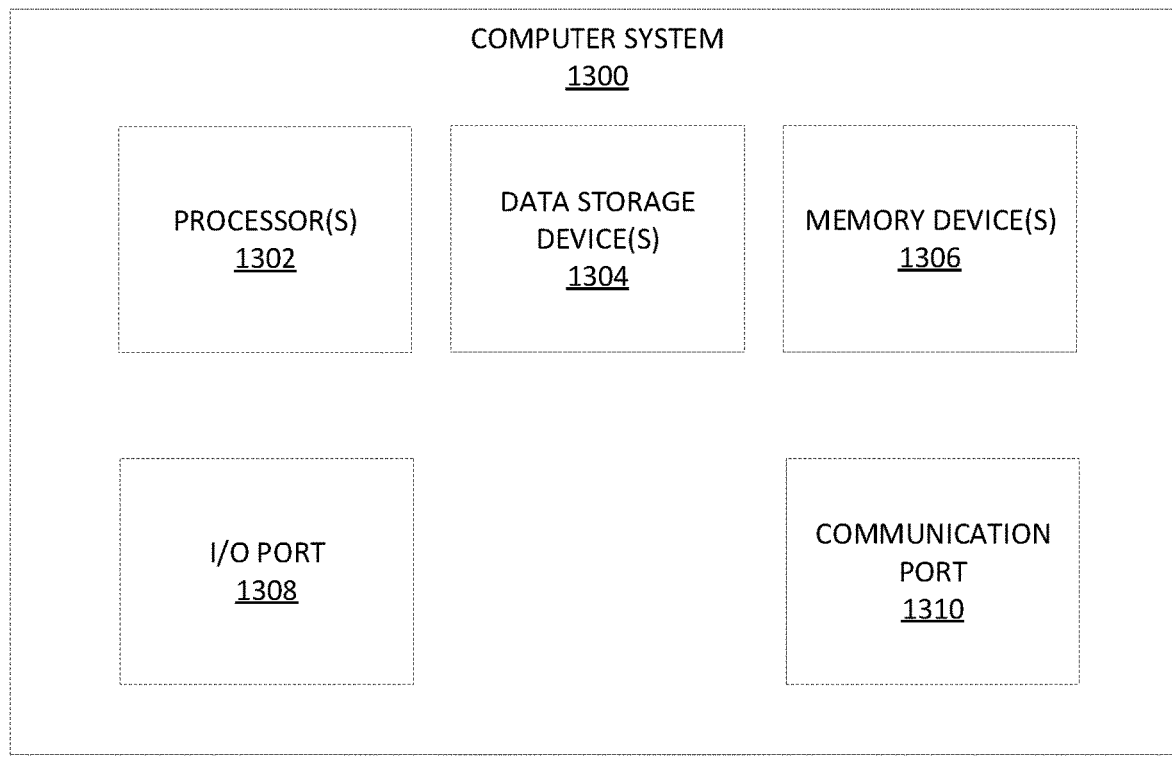
FIG. 13 is an example computing system having one or more computing units that may implement various systems and methods discussed herein is provided.

Referring to FIG. 13, a detailed description of an example computing system 1300 having one or more computing units that may implement various systems and methods discussed herein is provided. The computing system 1300 may be applicable to any of the computers or systems utilized in the preoperative planning, registration, and postoperative analysis of the arthroplasty procedure, and other computing or network devices. It will be appreciated that specific implementations of these devices may be of differing possible specific computing architectures not all of which are specifically discussed herein but will be understood by those of ordinary skill in the art.

The computer system 1300 may be a computing system that is capable of executing a computer program product to execute a computer process. Data and program files may be input to the computer system 1300, which reads the files and executes the programs therein. Some of the elements of the computer system 1300 are shown in FIG. 13, including one or more hardware processors 1302, one or more data storage devices 1304, one or more memory devices 1308, and/or one or more ports 1308-1310. Additionally, other elements that will be recognized by those skilled in the art may be included in the computing system 1300 but are not explicitly depicted in FIG. 13 or discussed further herein. Various elements of the computer system 1300 may communicate with one another by way of one or more communication buses, point-to-point communication paths, or other communication means not explicitly depicted in FIG. 13.

The processor 1302 may include, for example, a central processing unit (CPU), a microprocessor, a microcontroller, a digital signal processor (DSP), and/or one or more internal levels of cache. There may be one or more processors 1302, such that the processor 1302 comprises a single central-processing unit, or a plurality of processing units capable of executing instructions and performing operations in parallel with each other, commonly referred to as a parallel processing environment.

The computer system 1300 may be a conventional computer, a distributed computer, or any other type of computer, such as one or more external computers made available via a cloud computing architecture. The presently described technology is optionally implemented in software stored on the data stored device(s) 1304, stored on the memory device(s) 1306, and/or communicated via one or more of the ports 1308-1310, thereby transforming the computer system 1300 in FIG. 13 to a special purpose machine for implementing the operations described herein. Examples of the computer system 1300 include personal computers, terminals, workstations, mobile phones, tablets, laptops, personal computers, multimedia consoles, gaming consoles, set top boxes, and the like.

The one or more data storage devices 1304 may include any non-volatile data storage device capable of storing data generated or employed within the computing system 1300, such as computer executable instructions for performing a computer process, which may include instructions of both application programs and an operating system (OS) that manages the various components of the computing system 1300. The data storage devices 1304 may include, without limitation, magnetic disk drives, optical disk drives, solid state drives (SSDs), flash drives, and the like. The data storage devices 1304 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1306 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1304 and/or the memory devices 1306, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1300 includes one or more ports, such as an input/output (I/O) port 1308 and a communication port 1310, for communicating with other computing, network, or vehicle devices. It will be appreciated that the ports 1308-1310 may be combined or separate and that more or fewer ports may be included in the computer system 1300.

The I/O port 1308 may be connected to an I/O device, or other device, by which information is input to or output from the computing system 1300. Such I/O devices may include, without limitation, one or more input devices, output devices, and/or other devices.

In one implementation, the input devices convert a human-generated signal, such as, human voice, physical movement, physical touch or pressure, and/or the like, into electrical signals as input data into the computing system 1300 via the I/O port 1308. Similarly, the output devices may convert electrical signals received from computing system 1300 via the I/O port 1308 into signals that may be sensed as output by a human, such as sound, light, and/or touch. The input device may be an alphanumeric input device, including alphanumeric and other keys for communicating information and/or command selections to the processor 1302 via the I/O port 1308. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

In one implementation, a communication port 1310 is connected to a network by way of which the computer system 1300 may receive network data useful in executing the methods and systems set out herein as well as transmitting information and network configuration changes determined thereby. Stated differently, the communication port 1310 connects the computer system 1300 to one or more communication interface devices configured to transmit and/or receive information between the computing system 1300 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1310 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1310 may communicate with an antenna or other link for electromagnetic signal transmission and/or reception.

In an example implementation, patient data, bone models (e.g., generic, patient specific), transformation software, registration software, implant models, and other software and other modules and services may be embodied by instructions stored on the data storage devices 1304 and/or the memory devices 1306 and executed by the processor 1302. The computer system 1300 may be integrated with or otherwise form part of the surgical system 100. The computer device or system 1300 may, for instance, include a processing device 1302 and a computer-readable medium with one or more executable instructions stored thereon. The processing device 1302 is configured to execute the instructions to perform certain operations. As disclosed herein, the operations may include receiving preoperative patient data including a patient bone model. The operations may further include receiving coordinate locations of a tracker array coupled to a registration tool. The registration tool may include an engagement structure having three planar contacting surfaces defining three reference planes and an extension structure extending from the three planar contacting surfaces. The engagement structure may be positioned relative to a patient bone in a unique pose that limits translation and rotation of the engagement structure relative to the bone. The operations may further include storing a registration position of the registration tool relative to the bone. The registration position may be stored in one or more of a database, in memory 1306, in a data storage device 1304, and in the computer-readable medium.

The system set forth in FIG. 13 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed herein, for example, those shown in FIGS. 6, 8, and 10, among others, may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure including any of the methods described herein may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

In general, while the embodiments described herein have been described with reference to particular embodiments, modifications can be made thereto without departing from the spirit and scope of the disclosure. Note also that the term "including" as used herein is intended to be inclusive, i.e. "including but not limited to."

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

What is claimed is:

1. A surgical registration tool configured for use in a surgical registration on a bone comprising a femur having a shaft portion and a femoral condyle, the femoral condyle including a distal portion, a posterior portion, a medial portion, and a lateral portion, the surgical registration tool comprising:

a bone engagement structure being a single-piece construction and non-patient-specific, the bone engagement structure comprising a distal abutment structure configured to contact the distal portion of the femoral condyle, at least one posterior abutment structure configured to contact the posterior portion of the femoral condyle, a side abutment structure, and an anterior abutment structure, the distal abutment structure comprising a distal planar surface, the at least one posterior abutment structure comprising at least one planar surface extending distally from the distal planar surface and positioned perpendicular to the distal planar surface, the side abutment structure comprising a planar surface extending distally from the distal planar surface and positioned perpendicular to the distal planar surface and the at least one planar surface, the planar surface of the side abutment structure configured to contact at least one of the medial or lateral portion of the femoral condyle, the anterior abutment structure extending distally from the distal planar surface and terminating at a distal tip configured to contact the shaft portion of the femur; and a tracker array operably coupled to the bone engagement structure, the tracker array configured to be tracked by a navigation system.

2. The surgical registration tool of claim 1, wherein the distal abutment structure comprises a top side, a bottom side opposite the top side, a first side, and a second side opposite the first side, wherein the at least one posterior abutment structure extends distally from the bottom side, the side abutment structure extends distally from the first side, and the anterior abutment structure extends distally from the top side.

3. The surgical registration tool of claim 2, wherein the second side is free from any distally extending structures.

4. The surgical registration tool of claim 1, wherein the distal abutment structure comprises a plurality of projections extending distally from the distal planar surface configured to extend through a cartilage surface to bone.

5. The surgical registration tool of claim 1, wherein the at least one posterior abutment structure comprises at least one longitudinal protrusion extending distally along the at least one planar surface and extending outward from the at least one planar surface.

6. The surgical registration tool of claim 5, wherein the at least one longitudinal protrusion comprises a knife edge configured to cut through a cartilage surface to bone.

7. The surgical registration tool of claim 1, wherein the at least one posterior abutment structure comprises a pair of posterior abutment structures spaced apart from each other.

8. The surgical registration tool of claim 1, wherein the distal planar surface of the distal abutment structure defines a first plane, the at least one planar surface of the at least one posterior abutment structure comprises two planar surfaces defining a second plane, and the planar surface of the side abutment structure defines a third plane, wherein the first, second, and third planes are mutually perpendicular to each other.

9. The surgical registration tool of claim 1, further comprising: an attachment structure coupled to the bone engagement structure and extending proximally therefrom, the tracker array coupled to the attachment structure.

* * * * *